US009234188B2

(12) United States Patent
Rebar et al.

(10) Patent No.: US 9,234,188 B2
(45) Date of Patent: *Jan. 12, 2016

(54) MODIFIED ZINC FINGER BINDING PROTEINS

(75) Inventors: Edward Rebar, El Cerrito, CA (US); Andrew Jamieson, San Francisco, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 944 days.

This patent is subject to a terminal disclaimer.

(21) Appl. No.: 11/485,946

(22) Filed: Jul. 13, 2006

(65) Prior Publication Data

US 2006/0246588 A1 Nov. 2, 2006

Related U.S. Application Data

(62) Division of application No. 10/055,711, filed on Jan. 22, 2002.

(60) Provisional application No. 60/263,445, filed on Jan. 22, 2001, provisional application No. 60/290,716, filed on May 11, 2001.

(51) Int. Cl.
*C12N 5/14* (2006.01)
*C12N 15/82* (2006.01)
*C12N 9/10* (2006.01)
*C07K 14/47* (2006.01)
*A61K 48/00* (2006.01)

(52) U.S. Cl.
CPC .......... *C12N 9/1007* (2013.01); *C07K 14/4702* (2013.01); *C12N 15/8216* (2013.01); *C12N 15/8217* (2013.01); *C12N 15/8243* (2013.01); *A61K 48/00* (2013.01); *C07K 2319/00* (2013.01); *C07K 2319/81* (2013.01)

(58) Field of Classification Search
None
See application file for complete search history.

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid et al. |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans |
| 5,597,693 A | 1/1997 | Evans et al. |
| 5,602,009 A | 2/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,814,618 A | 9/1998 | Bujard et al. |
| 5,830,721 A | 11/1998 | Stemmer et al. |
| 5,869,618 A | 2/1999 | Lippman et al. |
| 5,871,902 A | 2/1999 | Weininger et al. |
| 5,871,907 A | 2/1999 | Winter et al. |
| 5,880,333 A | 3/1999 | Goff et al. |
| 5,905,146 A | 5/1999 | Lecka-Czernik |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,004,941 A | 12/1999 | Bujard et al. |
| 6,007,988 A | 12/1999 | Choo et al. |
| 6,013,453 A * | 1/2000 | Choo et al. .......... 506/9 |
| 6,140,081 A | 10/2000 | Barbas |
| 6,140,466 A | 10/2000 | Barbas, III et al. |
| 6,160,091 A | 12/2000 | Peukart et al. |
| 6,242,568 B1 | 6/2001 | Barbas, III et al. |
| 6,270,990 B1 | 8/2001 | Anderson et al. |
| 6,326,166 B1 | 12/2001 | Pomerantz et al. |
| 6,326,486 B1 | 12/2001 | Hogan et al. |
| 6,479,626 B1 * | 11/2002 | Kim et al. .......... 530/300 |

(Continued)

FOREIGN PATENT DOCUMENTS

| | | |
|---|---|---|
| EP | 0 875 567 A2 | 11/1998 |
| WO | WO 92/02536 | 2/1992 |
| WO | WO 95/11922 | 5/1995 |

(Continued)

OTHER PUBLICATIONS

Verma et al. Gene therapy—promises, problems and prospects. Nature, vol. 389, pp. 239-242, 1997.*
Palu et al. In pursuit of new developments for gene therapy of human diseases. J. Biotechnol. vol. 68, pp. 1-13, 1999.*
Luo et al. Synthetic DNA delivery systems. Nature Biotechnology, vol. 18, pp. 33-37, 2000.*
Verma and Weitzman, Gene Therapy: Twenty-first century medicine. Annual Review of Biochemistry, vol. 74, pp. 711-738, 2005.*
Filippova et al. An exceptionally conserved transcriptional repressor, CTCF, employs different combinations of zinc fingers to bind diverged promoter sequences of avian and mammalian c-myc oncogenes. Molecular and Cellular Biology, vol. 16, No. 6, pp. 2802-2813, Jun. 1996.*
Shiraishi et al. Exchange of histidine spacing between Sp1 and GLI zinc fingers: distinct effect of histidine spacing-linker region on DNA binding. Biochemistry, vol. 43, pp. 6352-6359, Apr. 2004.*

(Continued)

*Primary Examiner* — Brent T Page
*Assistant Examiner* — Matthew Keogh
(74) *Attorney, Agent, or Firm* — Pasternak Patent Law; Susan Abrahamson

(57) ABSTRACT

Disclosed herein are compositions and method comprising non-canonical (e.g., non-C2H2) zinc finger proteins.

6 Claims, 5 Drawing Sheets

(56) References Cited

U.S. PATENT DOCUMENTS

| | | | |
|---|---|---|---|
| 7,151,201 B2* | 12/2006 | Barbas et al. | 800/278 |
| 7,273,923 B2* | 9/2007 | Jamieson et al. | 530/370 |

FOREIGN PATENT DOCUMENTS

| | | |
|---|---|---|
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/27092 | 6/1999 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 00/41566 | 7/2000 |
| WO | WO 00/42219 A1 | 7/2000 |
| WO | WO 01/04296 A1 | 1/2001 |
| WO | WO 02/066640 A2 | 8/2002 |
| WO | WO 03/016496 A2 | 2/2003 |

OTHER PUBLICATIONS

Shiraishi et al. Swapping of the beta-hairpin region between Sp1 and GLI zinc fingers: significant role of the beta-hairpin region in DNA binding properties of C2H2-type zinc finger peptides. Biochemistry, vol. 44, pp. 2523-2228, Jan. 2005.*
Krizek et al. A consensus zinc finger peptide: Design, high-affinty metal binding, a pH-dependent structure, and a His to Cys sequence variant. Journal of the American Chemical Society, vol. 113, pp. 4518-4523, 1991.*
Roehm et al. Selectivity of methylation of metal-bound cysteinates and its consequences. Journal of the American Chemical Society, vol. 120, pp. 13083-13087, 1998.*
Agarwal et al., "Stimulation of Transcript Elongation Requires Both the Zinc Finger and RNA Polymerase II Binding Domains of Human TFIIS," Biochemistry 30(31): 7842-7851 (1991).
Antao et al., "A Thermodynamic Study of Unusually Stable RNA and DNA Hairpins," Nuc. Acids. Res. 19(21): 5901-5905 (1991).
Barbas, C.F. "Recent Advances in Phage Display," Curr. Opin. Biotech. 4: 526-530 (1993).
Barbas et al., "Assembly of Combinatorial Antibody Libraries on Phage Surfaces: The Gene III Site," PNAS 88: 7978-7982 (1991).
Barbas et al., "Semisynthetic Combinatorial Antibody Libraries: A Chemical Solution to the Diversity Problem," PNAS 89: 4457-4461 (1992).
Beerli et al., "Toward Controlling Gene Expression at Will: Specific Regulation of the ERBB-2/HER-2 Promoter by Using Polydactyl Zinc Finger Proteins Constructed From Modular Building Blocks," PNAS 95: 14628-14633 (1998).
Beerli et al., "Positive and Negative Regulation of Endogenous Genes by Designed Transcription Factors," PNAS 97: 1495-1500 (2000).
Bellefroid et al., "Clustered Organization of Homologous Krab Zinc-Finger Genes With Enhanced Expressoin in Human T Lymphoid Cells," EMBO J. 12(4): 1363-1374 (1993).
Berg, J.M., "DNA Binding Specificity of Steroid Receptors," Cell 57: 1065-1068 (1989).
Berg, J.M., "SP1 and the Subfamily of Zinc-Finger Proteins With Guanine-Rich Binding Sites," PNAS 89: 11109-11110 (1992).
Berg et al., "The Galvanization of Biology: A Growing Appreciation for the Roles of Zinc," Science 271: 1081-1085 (1996).
Berg, J.M., "Letting Your Fingers do the Walking," Nature Biotechnology 15: 323 (1997).
Bergqvist et al., "Loss of DNA-Binding and New Transcriptiional Trans-Activation Function in Polyomavirus Large T-Antigen With Mutation of Zinc Finger Motif," Nature Biotechnology 18(9): 2715-2720 (1990).
Blaese et al., "Vectors in Cancer Therapy: How Will They Deliver?" Cancer Gene Therapy 2(4): 291-297 (1995).
Blackburn, "Engineering and Design: Rational Versus Combinatorial Approaches," Curr. Opin. Struct. Biol. 10:399-400 (2000).
Bonde et al., "Ontogeny of the V-ERBA Oncoprotein From the Thyroid Hormone Receptor: An Alteration in the DNA Binding Domain Plays a Role Crucial for Verba Function," J. Virology 65(4): 2037-2046 (1991).
Caponigro et al., "Transdominant Genetic Analysis of a Growth Control Pathway," PNAS 95: 7508-7513 (1998).
Celenza et al., "A Yeast Gene That is Essential for Release From Glucose Repression Encodes a Protein Kinase," Science 233: 1175-1180 (1986).
Cheng et al., "Identification of Potential Target Genes for ADRLP Through Characterization of Essential Nucleotides in UAS1," Mol. Cellular Biol. 14(6): 3842-3852 (1994).
Cheng et al., "A Single Amino Acid Subsitution in Zinc Finger 2 of ADRLP Changes Its Binding Specificity at Two Positions in UAS1," J. Mol. Boil. 251: 1-8 (1995).
Choo et al., "Designing DNA-Binding Proteins on the Surface of Filamentous Phage," Curr. Opin. Biotechnology 6: 431-436 (1995).
Choo et al., "Physicial Basis of Protein-DNA Recognition Code," Curr. Opin. Struct. Biol. 7(1): 117-125 (1997).
Choo et al., "Promoter-Specific Activiation of Gene Expression Directed by Bacteriophage-Selected Zinc Fingers," J. Mol. Biol. 273: 525-532 (1997).
Choo et al., "In Vivo Repression by a Site-Specific DNA-Binding Protein Deisned Against an Onogenic Sequence," Nature 372: 642-645 (1994).
Choo et al., "All Wrapped Up," Nature Struct. Biol. 5(4): 253-255 (1998).
Choo, Y., "Recognition of DNA Methylation by Zinc Fingers," Nature Struct. Biol. 5(4): 264-265 (1998).
Choo, Y., "End Effects in DNA Recognition Code," Nuc. Acids. Res. 26(2): 554-557 (1998).
Choo et al., "A Role in DNA-Binding for the Linker Sequences of the First Three Zinc Fingers of TFIIIA" Nuc. Acids Res. 21(15): 3341-3346 (1993).
Choo et al., "Toward a Code for the Interactions of Zinc Fingers With DNA: Selection of Randomized Fingers Displayed on Phage," PNAS 91: 11163-11167 (1994).
Choo et al., "Selection of DNA Binding Sites for Zinc Fingers Using Randomized DNAS Reveals Coded Interactions," PNAS 91: 11168-11172 (1994).
Choo et al., "Advances in Zinc Finger Engineering," Curr. Opin. Struct. Biol. 10:411-416 (2000).
Clarke et al., "Zinc Fingers in Caenorhabditis Elegans: Finding Familiies and Probing Patheways," Science 282: 2018-2022 (1998).
Clemens, et al., "Relative Contributions of the Zinc Fingers of Transcription Factor IIIA to the Energetics of DNA Building," J. Mol. Biol. 244:23-35 (1994).
Corbi et al., "Synthesis of a New Zinc Finger Peptide: Comparison of Its "Code" Deduced and "Casting" Derived Binding Sites," FEBS Letters 417: 71-74 (1997).
Crozatier et al., "Single Amino Acid Exchanges in Separate Domains of the *Drosophilia* Serendipity Zinc Finger Protein Cause Embroyonic and Sex Biased Lethality," Genetics 131: 905-916 (1992).
Debs et al., "Regulation of Gene Expression In Vivo by Liposome-Mediated Delivery of a Purified Transcription Factor," J. Biological Chemistry 265(18): 10189-10192 (1990).
DesJardins et al., "Repeated CT Elements Bound by Zinc Finger Proteins Control the Absolute and Relative Activities of the Two Principal Human C-MYC Promoters," Mol. Cell. Biol. 13(9): 5710-5724 (1993).

(56) References Cited

OTHER PUBLICATIONS

Desjarlais et al., "Redesigning the DNA-Binding Specificity of a Zinc Finger Protein: A Data Base-Guided Approach," Proteins: Structure, Function, and Genetics 12(2): 101-104 (1992).
Desjarlais et al., "Redesigning the DNA-Binding Specificity of a Zinc Finger Protein: A Data Base-Guided Approach," Proteins: Structure, Function, and Genetics 13(2): 272 (1992).
Desjarlais et al., "Toward Rules Relating Zinc Finger Protein Sequences and DNA Binding Site Preferences," *Proc Natl Acad Sci USA* 89:7345-7349 (1992).
Desjarlais et al., "Use of a Zinc-Finger Consensus Sequences Framework and Specificity Rules to Design Specific DNA Binding, Proteins" PNAS 90: 2256-2260 (1993).
Desjarlais et al., "Length-Encoded Multiplex Binding Site Determination: Application to Zinc Finger Proteins," PNAS 91: 11099-11103 (1994).
Dibello et al., "The *Drosophila* Broad-Complex Encodes a Family of Related Proteins Containing Zinc Fingers," Genetics 129: 385-397 (1991).
Donze et al., "Activation of Delta-Globin Gene Expression by Erythroid Krupple-Like Factor: A Potential Approach for Gene Therapy of Sickle Cell Disease," Blood 88: 4051-4057 (1996).
Edelstein et al., "Gene Therapy Clinical Trials Worldwide 1989-2004—An Overview," J. Gene Med 6:597-602 (2004).
Elrod-Erickson et al., "ZIF268 Protein-DNA Complex Refined at 1.6: A Model System for Understanding Zinc Finger-DNA Interactions," Structure 4(10): 1171-1180 (1996).
Elrod-Erickson et al., "High-Resolution Structures of Variant ZIF268-DNA Complexes: Implications for Understanding Zinc Finger-DNA Recognition," Structure 6(4): 451-464 (1998).
Fairall et al., "The Crystal Structure of a Two Zinc-Finger Peptide Reveals an Extension to the Rules for Zinc-Finger/DNA Recognition," Nature 366: 483-487 (1993).
Fox et al., "Transcriptional Cofactors of the Fog Family Interact With Gata Proteins by Means of Multiple Zinc Fingers," EMBO J. 18:2812-2822 (1999).
Frankel et al., "Fingering Too Many Proteins," Cell 53: 675 (1988).
Friesen et al., "Phage Display of RNA Binding Zinc Fingers From Transcription Factor 11A," J. Biological Chem. 272(17): 10994-10997 (1997).
Friesen et al., "Specific RNA Binding Proteins Constructed From Zinc Fingers," Nature Structural Biology 5(7): 543-546 (1998).
Ghosh, "A Relational Database of Transcription Factors," Nucleic Acids Res. 18: 1749-1756 (1990).
Gillemans et al., "Altered DNA Binding Specificity Mutants of EKLF and SPL Show That EKLF is an Activator of the B-Globin Locus Control Region In Vivo," Genes and Development 12: 2863-2873 (1998).
Gogos et al., "Recognition of Diverse Sequences by Class 1 Zinc Fingers: Asymmetries and Indirect Effects on Specificty in the Interaction Between CF2II and A+T-Rich Sequences Elements," PNAS 93(5): 2159-2164 (1996).
Gossen et al., "Tight Control of Gene Expression in Mammalian Cells by Tetracycline-Responsive Promoter," PNAS 89:5547-5551 (1992).
Green et al., "Alteration of ZIF268 Zinc-Finger Motifs Gives Rise to Non-Native Zinc Coordination Sites but Preserves Wild-Type DNA Recognition," Biochem J. 333:85-90 (1998).
Greisman et al., "A General Strategy for Selecting High-Affinity Zinc Finger Proteins for Diverse DNA Target Sites," *Science* 275: 657-661 (1997).
Guyer et al., "Activation of Latent Transgenes in Arabidopsis Using a Hybrid Transcription Factor," Genetics 149:633-639 (1998).
Hall et al., "Functional Interaction Between the Two Zinc Finger Domains of the V-ERBA Oncoprotein," Cell Growth & Differentiation 3: 207-216 (1992).
Hamilton et al., "High Affinity Binding Sites for the Wilms' Tumor Suppressor Protein WTI," Nuc. Acids. Res. 23(2): 277-284 (1995).
Hamilton et al., "Comparison of the DNA Binding Characteristics of the Related Zinc Finger Proteins WT1 and EGR1" Biochemistry 37: 2051-2058 (1998).
Hanas et al., "Internal Deletion Mutants of Xenopus Transcription FACTOR IIIA," Nuc. Acids. Res. 17(23): 9861-9870 (1989).
Hard et al., "Solution Structure of the Glucocorticoid Receptor DNA-Binding Domain," Science 249:157-160 (1990).
Hayes et al., "Locations of Contacts Between Individual Zinc Fingers Xenopus Laevis Transcription Factor IIIA and the Internal Control Region of a 5S RNA Gene," Biochemistry 31: 11600-11605 (1992).
Heinzel et al., "A Complex Containing N-CoR, MSin3 and Histone Deacetylese Medates Transcriptional Repression," Nature 387: 43-48 (1997).
Hirst et al., "Discrimination of DNA Response Elements for Thyroid Hormone and Estrogen is Dependent on Dimerization of Receptor DNA Binding Domains," PNAS 89: 5527-5531 (1992).
Hoffman et al., "Structures of DNA-Binding Mutant Zinc Finger Domains: Implications for DNA Binding," Protein Science 2: 951-965 (1993).
Hori et al., "Artificial Zinc Finger Peptide Containing a Novel $HIS_4$ Domain," J. Am. Chem. Soc. 122:7648-7653 (2000).
Hori et al., "The Engineering, Structure, and DNA Binding Properties of a Novel $HIS_4$-Type Zinc Finger Peptide," Nucleic Acids Symposium Series No. 44, pp. 295-296 (2000).
Imhof et al., "Transcriptional Regulation of the AP-2ALPHA Promoter by BTEB-1 and AP-2REP, a Novel WT-1/EGR-Related Zinc Finger Repressor," Molecular and Cellular Biology 19(1): 194-204 (1999).
Isalan et al., "Synergy Between Adjacent Zinc Fingers in Sequence-Specific DNA Recognition," PNAS 94(11): 5617-5621 (1997).
Isalan et al., "Comprehensive DNA Recogniition Through Concerted Interactions From Adjacent Zinc Fingers," *Biochemistry* 37:12026-12033 (1998).
Jacobs, G. H., "Determination of the Base Recognition Positions of Zinc Fingers From Sequence Analysis," EMBO J. 11(12): 4507-4517 (1992).
Jamieson et al., "A Zinc Finger Directory for High-Affinity DNA Recognition," PNAS 93: 12834-12839 (1996).
Jamieson et al., "In Vitro Selection of Zinc Fingers With Altered DNA-Binding Specificity," *Biochemistry* 33:5689-5695 (1994).
Jiang et al., "A Novel Family of CYS-CYS, HIS-CYS Zinc Finger Transcription Factors Expressed in Developing Nervous System and Pituitary Gland," J. Biol. Chem. 271:10723-10730 (1996).
Jones et al., "Replacing the Complementarity-Determining Regions in a Human Antibody With Those From a Mouse," Nature 321: 522-525 (1986).
Julian et al., "Replacement of HIS23 by CYS in a Zinc Finger of HIV-1NCP7 Led to a Change in 1H NMR-Derived 3D Structure and to a Loss of Biological Activity," FEBS Letters 331(1,2): 43-48 (1993).
Kamiuchi et al., "New Multi Zinc Finger Protein: Biosynthetic Design and Characteristics of DNA Recognition," Nucleic Acids Symposium Series 37: 153-154 (1997).
Kang et al., "Zinc Finger Proteins as Designer Transcription Factors," *J.Biol Chem* 245(12):8742-8748 (2000).
Kim et al., "Serine at Position 2 in the DNA Recognition Helix of a CYS2-HIS2 Zinc Finger Peptide is Not, In General, Responsible for Base Recognition," J. Mol. Biol. 252: 1-5 (1995).
Kim et al., "Site-Specific Cleavage of DNA-RNA Hybrids by Zinc Finger/Foki/Cleavage Domain Fusions," Gene 203: 43-49 (1997).
Kim et al., "A 2.2 A° Resolution Crystal Structure of a Designed Zinc Finger Protein Bound to DNA," Nat. Struct. Biol. 3(11): 940-945 (1996).
Kim et al., "Design of Tata Box-Binding Protein/Zinc Finger Fusions for Targeted Regulation of Gene Expression," PNAS 94: 3616-3620 (1997).
Kim et al., "Hybrid Restriction Enzymes: Zinc Finger Fusions FOK 1 Cleavage Domain," PNAS 93: 1156-1160 (1996).
Kim et al., "Transcriptional Repression by Zinc Finger Peptides. Exploring the Potential for Applications in Gene Therapy" J. Biol. Chem. 272: 29795-29800 (1997).

(56) References Cited

OTHER PUBLICATIONS

Kim et al., "Getting a Handhold on DNA: Design of Poly-Zinc Finger Proteins With Femtomolar Dissociation Constants," *Proc Natl Acad Sci USA* 95:2812-2817 (1998).

Kinzler et al., "The GLI Gene is Member of the Kruppel Family of Zinc Finger Proteins," Nature 332: 371-374 (1988).

Klug, A. "Gene Regulatory Proteins and Their Interaction With DNA," Ann. NY Acad. Sci. 758: 143-160 (1995).

Klug et al., "Protein Motifs 5: Zinc Fingers," FASEB J. 9: 597-604 (1995).

Klug, "Zinc Finger Peptides for the Regulation of Gene Expression," J. Mol. Biol. 293: 215-218 (1999).

Kochoyan et al., "Alternating Zinc Fingers in the Human Male Associated Protein ZFY:2D NMR Structure of an Even Finger and Implications for "Jumping-Linker" DNA Recognition," Biochemistry 30:3371-3386.

Kothekar, "Computer Simulation of Zinc Finger Motif From Cellular Nucleic Acid Binding Proteins and Their Interaction With Consensus DNA Sequences," FEBS Letters 274(1,2): 217-222 (1990), 1991.

Kriwacki et al., "Sequence-Specific Recognition of DNA by Zinc Finger Peptides Derived From the Transcription Factor SP-1," PNAS 89: 9759-9763 (1992).

Krizek et al., "Ligand Variation and Metal Ion Binding Specificity in Zinc Finger Peptides," Inorg. Chem. 32:937-940 (1993).

Kudla et al., "The Regulatory Gene Area Mediating Nitrogen Metabolite R in Aspergillus Nidulans Mutations Affecting Specificity of Gene Activation Alter a Loop Residue of Putative Zinc Finger," EMBO J. 9(5): 1355-1364 (1990).

Laird-Offringa et al., "RNA-Binding Proteins Tamed," Nat. Structural Biol. 5(8): 665-668 (1998).

Lee et al., Three-Dimensional Solution Structure of a Single Zinc Finger DNA-Binding Domain, Science 245:635-637 (1991).

Liu et al., "Design of Polydactyl Zinc-Finger Proteins for Unique Addressing Within Complex Genomes," PNAS 94: 5525-5530 (1997).

Liu et al., "Transcription Factor EGR-1 Suppresses the Growth and Transformation of Human HT-1080 Fibrosarcoma Cells by Induction of Transforming Growth Factor Beta 1," PNAS 93(21): 11831-11836 (1996).

Liu et al., "Regulation of an Endogenous Locus Using a Panel of Designed Zinc Finger Proteins Targeted to Accessible Chromatin Regions," *J Biol Chem* 276:11323-11334 (2001).

Luo et al., "Synthetic DNA Delivery Systems," Nat Biotechnol 18:33-37 (2000).

Mandel-Gutfreund et al., "Quantitative Parameters for Amino Acid-Base Interaction: Implication for Predication of Protein-DNA Binding Sites," Nuc. Acids Res. 26(10): 2306-2312 (1998).

Margolin et al., "Kruppel-Associated Boxes are Potent Transcriptional Repression Domains," PNAS 91: 4509-4513 (1994).

Matheny, et al., "The Nuclear Localization Signal of NGFI-A is Located Within the Zinc Finger DNA Binding Domain," The Journal of Biological Chemistry 269(11): 8176-8181 (1994).

Merkle et al., "Design and Characterization of a Ligand-Binding Metallopeptide," J. Am. Chem. Soc. 113:5450-5451 (1991).

Miesfeld et al., "Glucocorticoid Receptor Mutants That Define a Small Region Sufficient for Enhancer Activation," Science 236:423-427 (1987).

Miura et al., "Role of Metal-Ligand Coordination in the Folding Pathway of Zinc Finger Peptides," Biochim. Biophys. Acta 1384:171-179 (1998).

Mizushima et al., "PEF-BOS, A Powerful Mammilian Expression Vector," Nuc. Acids. Res. 18(17): 5322 (1990).

Mukhopadhyay et al., "The Von Hippel-Lindau Tumor Suppressor Gene Product Interacts With SP1 to Repress Vascular Endothelial Growth Factor Promoter Activity" Mol. Cell. Biol. 17(9): 5629-5639 (1997).

Nakagama et al, "Sequence and Structural Requirements for High-Affinity DNA Binding by the WT1 Gene Product," Molecular and Cellular Biology 15(3): 1489-1498 (1995).

Nardelli et al., "Zinc Finger-DNA Recognition: Analysis of Base Specificity by Site-Directed Mutagenesis," Nucleic Acids Research 20(16): 4137-4144 (1992).

Nardelli et al., "Base Sequence Discrimination by Zinc-Finger DNA-Binding Domains," Nature 349: 175-178 (1991).

Nekludova et al., "Distinctive DNA Conformation With Enlarged Major Groove is Found in Znfinger-DNA and Other Protein-DNA Complexes," PNAS 91: 6948-6952 (1994).

Omichinski et al., "High-Resolution Three-Dimensional Structure of a Single Zinc Finger From a Human Enhancer Binding Protein in Solution," Biochemistry 29:9324-9334 (1990).

Orkin et al., "Report and Recommendations of the Panel to Assess the NIH Investment in Research on Gene Therapy," (Dec. 7, 1995).

Pabo et al., "Systematic Analysis of Possible Hydrogen Bonds Between Amino Acid Side Chains and B-Form DNA," J. Biomolecular Struct. Dynamic 1: 1039-1049 (1983).

Pabo et al., Protein-DNA Recognition, Ann. Rev. Biochem. 53: 293-321 (1984).

Pabo, C.O., "Transcription Factors: Structural Families and Principles of DNA Recognition," Ann. Rev. Biochem. 61: 1053-1095 (1992).

Palu et al., "In Pursuit of New Developments for Gene Therapy of Human Diseases," J. Biotechnol 68:1-13 (1999).

Park et al., "Design and Synthesis of a New Peptide Recognizing a Specific 16-Base-Pair Site of DNA," J. Am. Chem. Soc. 117:6287-6291 (1995).

Pavletich et al., "Crystal Structure of a Five-Finger GLI-DNA Complex: New Perspectives on Zinc Fingers," Science, 261: 1701-1707 (1993).

Pavletich et al., "Zinc Finger-DNA Recognition: Crystal Structure of a ZIF268-DNA Complex at 2.1 A," Science 252:809-817 (1991).

Pengue et al., "Repression of Transcriptional Activity at a Distance by the Evolutionarily Conserved Krab Domain Present in a Subfamily of Zinc Finger Proteins," Nuc. Acids Res. 22(15): 2908-2914 (1994).

Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," J. Virology 69(10): 6577-6580 (1995).

Pengue et al., "Kruppel-Associated Box-Mediated Repression of RNA Polymerase II Promoters is Influenced by the Arrangement of Basal Promoter Elements," PNAS 93: 1015-1020 (1996).

Pomerantz et al., "Analysis of Homeodomain Function by Structure-Based Design of a Transcription Factor," PNAS 92: 9752-9756 (1995).

Pomerantz et al., "Structure-Based Designed of a Dimeric Zinc Finger Protein," Biochemistry 37(4): 965-970 (1998).

Pomerantz et al., "Structure-Based Design of Transcription Factors," Science 267: 93-96 (1995).

Qian et al., "Two-Dimensional NMR Studies of the Zinc Finger Motif: Solution Structures and Dynamics of Mutant ZFY Domains Containing Aromatic Substitutions in the Hydrophobic Core," Biochemistry 31:7463-7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," Molecular Endocrinology 6(7): 1103-1112 (1992).

Rauscher et al., "Binding of the Wilms' Tumor Locus Zinc Finger Protein to the EGR-I Consensus Sequence," Science 250: 1259-1262 (1990).

Ray et al., "Repressor to Activator Switch by Mutations in the First Zn Finger of the Glucocorticoid Receptor: Is Direct DNA Binding Necessary?" PNAS 88: 7086-7090 (1991).

Rebar et al., "Phage Display Methods for Selecting Zinc Finger Proteins With Novel DNA-Binding Specificities," Methods in Enzymology 267: 129-149 (1996).

Rebar et al, "Zinc Finger Phage: Affinity Selection of Fingers With New DNA-Binding Specifities," Science 263: 671-673 (1994).

Reith et al, "Cloning of the Major Histocompatibility Complex Class II Promoter Binding Protein Affected in a Hereditary Defect in Class II Gene Regulation," PNAS 86: 4200-4204 (1989).

(56) References Cited

OTHER PUBLICATIONS

Rhodes et al., "Zinc Fingers: They Play a Key Part in Regulating the Activity of Genes in Many Species, From Yeast to Humans. Fewer Than 10 Years Ago No on Knew They Existed." Scientific American 268:56-65 (1993).
Rice et al., "Inhibitors of HIV Nucleocapsid Protein Zinc Fingers as Candidates for the Treatment of AIDS," Science 270: 1194-1197 (1995).
Rivera et al., "A Humanized System for Pharmacologic Control of Gene Expression," Nature Medicine 2(9): 1028-1032 (1996).
Rollins et al., "Role of TFIIIA Zinc Fingers In Vivo: Analysis of Single-Finger Function in Developing Xenopus Embryos," Molecular Cellular Biology 13(8): 4776-4783 (1993).
Sadowski et al., "GAL4-VP16 is an Unusually Potent Transcriptional Activator," Nature 335: 563-568 (1988).
Saleh et al., "A Novel Zinc Finger Gene on Human Chromosome 1 QTER That is Alternatively Spliced in Human Tissues and Cell Lines," American Journal of Human Genetics 52: 192-203 (1993).
Schena et al., "A Steroid-Inducible Gene Expression System for Plant Cells," PNAS 88:10421-10425 (1991).
Segal et al., "Design of Novel Sequences-Specific DNA-Binding Proteins," Curr. Opin. Chem. Biol. 4:34-39 (2000).
Shi et al., "Specific DNA-RNA Hybrid Binding by Zinc Finger Proteins," Science 268: 282-284 (1995).
Shi et al., "DNA Unwinding Induced by Zinc Finger Protein Binding," Biochemistry 35: 3845-3848 (1996).
Shi et al., "A Direct Comparison of the Properties of Natural and Designed Finger Proteins," Chem. & Biol. 2(2): 83-89 (1995).
Singh et al., "Molecular Cloning of an Enhancer Binding Protein: Isolation by Screening of an Expression Library With a Recognition Site DNA," Cell 52: 415-423 (1988).
Skerka et al., "Coordinate Expression and Distinct DNA-Binding Characteristics of the Four EGR-Zinc Finger Proteins in Jurkat T Lymphocytes," Immunobiology 198: 179-191 (1997).
South et al., "The Nucleocapsid Protein Isolated From HIV-1 Particles Binds Zinc and Forms Retroviral-Type Zinc Fingers," Biochemistry 29: 7786-7789 (1990).
Spengler et al., "Regulation of Apoptosis and Cell Cycle Arrest by ZAC1, A Novel Zinc Finger Protein Expressed in the Pituitary Gland and the Brain," EMBO J. 16(10): 2814-2825 (1997).
Suzuki et al., "Stereochemical Basis of DNA Recognition by Zn Fingers," Nuc. Acids Res. 22(16): 3397-3405 (1994).
Suzuki et al., "DNA Recognition Code of Transcriptional Factors in the Helix-Turn-Helix, Probe Helix, Hormone Receptor, and Zinc Finger Families," PNAS 91: 12357-12361 (1994).
Swimoff et al, "DNA-Binding Specificity of NGFI-A and Related Zinc Finger Transcriptional Factors," Mol. Cell. Biol. 15(14): 2275-2287 (1995).
Takatsuji, H., "Zinc-Finger Transcription Factors in Plants," CMLS Cell, Mol. Life Sci. 54:582-596 (1998).
Taylor et al., "Designing Zinc-Finger ADRI Mutants With Altered Specificity of DNA Binding to T in UASI Sequences," Biochemistry 34: 3222-3230 (1995).
Thiesen et al., "Amino Acid Substitutions in the SP1 Zinc Finger Domain Alter the DNA Binding Affinity to Cognate SP1 Target Site," Biochem. Biophys. Res. Communications 175(1): 333-338 (1991).
Thiesen et al., "Determination of DNA Binding Specificities of Mutated Zinc Finger Domains," FEBS letters 283(1): 23-26 (1991).
Thiesen H. J. "From Repression Domains to Designer Zinc Finger Proteins: A Novel Strategy for Intracellular Immunization Against HIV," Gene Expression 5: 229-243 (1996).
Thukral et al., "Localization of a Minimal Binding Domain and Activation Regions in Yeast Regulatory Protein ADR11 ," Molecular Cellular Biology 9(6): 2360-2369 (1989).
Thukral et al., "Two Monomers of Yeast Transcription Factor ADR1 Bind A Paldromic Sequence Symmetrically to Activate ADH2 Expression," Molecular Cellular Biol. 11(3): 1566-1577 (1991).
Thukral et al., "Mutations in the Zinc Fingers of ADR1 That Change the Specificity of DNA Binding and Transactivation," Mol. Cell. Biol. 12(6): 2784-2792 (1992).
Thukral et al., "Alanine Scanning Site-Directed Mutagenesis of the Zinc Fingers of Transcription Factor ADR1: Residues That Contact DNA and That Transactivate," PNAS 88: 9188-9192 (1991).
Verma et al., "Gene Therapy—Promises, Problems and Prospects," Nature 389:239-242 (1998).
Vortkamp et al., "Identification of Optimized Target Sequences for the GL 13 Zinc Finger Protein," DNA Cell Biol. 14(7): 629-634 (1995).
Wang et al., "Dimerization of Zinc Fingers Mediated by Peptides Evolved In Vitro From Random Sequences," PNAS 96: 9568-9573 (1999).
Webster et al., "Conversion of the E1A a CYS4 Zinc Finger to a Nonfunctional HIS2, CYS2 Zinc Finger by a Single Point Mutation," PNAS 88: 9989-9993 (1999).
Whyatt et al., "The Two Zinc Finger-Like Domains of GATA-1 Have Different DNA Binding Specificities," EMBO J. 12(13): 4993-5005 (1993).
Wilson et al., "In Vivo Mutational Analysis of the NGFI-A Zinc Fingers," J. Biol. Chem. 267(6): 3718-3724 (1992).
Witzgall et al., "The Kruppel-Associated Box-A (Krab-A) Domain of Zinc Finger Proteins Mediates Transcriptional Repression," PNAS 91: 4514-4518 (1994).
Wolfe et al., "Analysis of Zinc Fingers Optimized via Phage Display: Evaluating the Utility of a Recognition Code," J. Mol. Biol. 285: 1917-1934 (1999).
Wright et al., "Expression of a Zinc Finger Gene in HTLV-I and HTLV-II Transformed Cell," Science 248:588-591 (1990).
Wu et al., "Human Immunodeficiency Virus Type 1 Nucleocapsid Protein Reduces Reverse Transcriptase Pausing at a Secondary Structure Near the Murine Leukemia Virus Polypurine Tract," J. Virol. 70(10): 7132-7142 (1996).
Wu et al., "Building Zinc Fingers by Selection: Toward a Therapeutic Application," PNAS 92: 344-348 (1995).
Wuttke, Deborah S., et al., "Solution Structure of the First Three Zinc Fingers of TFIIIA Bound to the Cognate DNA Sequence: Determinants of Affinity and Sequence Specificity," J. Mol. Biol. 273:183-206 (1997).
Yang et al., "Surface Plasmon Resonance Based Kinetic Studies of Zinc Finger-DNA Interaction," J. Immunol. Methods 183: 175-182 (1995).
Yu et al., "A Hairpin Ribozyme Inhibits Expression of Diverse Strains of Human Immunodeficiency Virus Type 1," PNAS 90: 6340-6344 (1993).
Zhang et al., "Synthetic Zinc Finger Transcription Factor Action at an Endogenous Chromosomal Site. Activation of the Human Erythropoietin Gene," Journal of Biological Chemistry 275(43): 33850-33860 (2000).

* cited by examiner

MODIFIED ZINC FINGER BINDING PROTEINS

CROSS REFERENCE TO RELATED APPLICATIONS

This application is a divisional of U.S. patent application Ser. No. 10/055,711 filed Jan. 22, 2002. Said U.S. patent application Ser. No. 10/055,711 claims the benefit of U.S. provisional patent application Ser. No. 60/263,445 filed Jan. 22, 2001 and also claims the benefit of U.S. provisional patent application Ser. No. 60/290,716 filed May 11, 2001. The disclosures of all of the aforementioned applications are incorporated by reference in their entireties for all purposes.

TECHNICAL FIELD

The methods and compositions disclosed herein relate generally to the field of regulation of gene expression and specifically to methods of modulating gene expression by utilizing polypeptides derived from zinc finger-nucleotide binding proteins.

BACKGROUND

Sequence-specific binding of proteins to DNA, RNA, protein and other molecules is involved in a number of cellular processes such as, for example, transcription, replication, chromatin structure, recombination, DNA repair, RNA processing and translation. The binding specificity of cellular binding proteins that participate in protein-DNA, protein-RNA and protein-protein interactions contributes to development, differentiation and homeostasis. Alterations in specific protein interactions can be involved in various types of pathologies such as, for example, cancer, cardiovascular disease and infection.

Zinc finger proteins (ZFPs) are proteins that can bind to DNA in a sequence-specific manner. Zinc fingers were first identified in the transcription factor TFIIIA from the oocytes of the African clawed toad, Xenopus laevis. A single zinc finger domain of this class of ZFPs is about 30 amino acids in length, and several structural studies have demonstrated that it contains a beta turn (containing the two invariant cysteine residues) and an alpha helix (containing the two invariant histidine residues), which are held in a particular conformation through coordination of a zinc atom by the two cysteines and the two histidines. This class of ZFPs is also known as C2H2 ZFPs. Additional classes of ZFPs have also been suggested. (See, e.g., Jiang et al. (1996) J. Biol. Chem. 271: 10723-10730 for a discussion of Cys-Cys-His-Cys (C3H) ZPFs.) To date, over 10,000 zinc finger sequences have been identified in several thousand known or putative transcription factors. Zinc finger domains are involved not only in DNA recognition, but also in RNA binding and in protein-protein binding. Current estimates are that this class of molecules will constitute about 2% of all human genes.

Most zinc finger proteins have conserved cysteine and histidine residues that tetrahedrally-coordinate the single zinc atom in each finger domain. In particular, most ZFPs are characterized by finger components of the general sequence: -Cys-$(X)_{2-4}$-Cys-$(X)_{12}$-His-$(X)_{3-5}$-His (SEQ ID NO: 1), where X is any amino acid (the C2H2 ZFPs). The zinc-coordinating sequences of this most widely represented class contain two cysteines and two histidines with particular spacings, for example zinc fingers found in the yeast protein ADRI, the human male associated protein ZFY, the HIV enhancer protein and the Xenopus protein Xfin have been solved by high resolution NMR methods (Kochoyan, et al., Biochemistry, 30:3371-3386, 1991; Omichinski, et al., Biochemistry, 29:9324-9334, 1990; Lee, et al., Science, 245:635-637, 1989). Based on x-ray crystallography, the three-dimensional structure of a three finger polypeptide-DNA complex derived from the mouse immediate early protein zif268 (also known as Krox-24) has been solved. (Pavletich and Pabo, Science, 252:809-817, 1991). The folded structure of each finger contains an antiparallel β-turn, a finger tip region and a short amphipathic α-helix. The metal coordinating ligands bind to the Zn ion and, in the case of zif268 zinc fingers, the short amphipathic α-helix binds in the major groove of DNA. In addition, the conserved hydrophobic amino acids and zinc coordination by the cysteine and histidine residues stabilize the structure of the individual finger domain.

The folding of a C2H2 ZFP into the proper finger structure can be entirely disrupted by exchange of the C2H2 ligand amino acids. Miura et al. (1998) Biochim. Biophys. Acta 1384:171-179. Furthermore, metal binding specificity of peptides based on the C2H2 consensus sequence can be altered. Krizek et al. (1993) Inorg. Chem. 32:937-940; Merkle et al. (1991) J. Am Chem. Soc. 113:5450-5451. Although detailed models for the interaction of zinc fingers and DNA have also been proposed (Berg, 1988; Berg, 1990; Churchill, et al., 1990), mutations in finger 2 of the three-fingered C2H2 ZFP zif268 have been shown to entirely abolish DNA binding (Green et al. (1998) Biochem J. 333:85-90).

Nonetheless, increased understanding of the nature and mechanism of protein binding specificity has encouraged the hope that specificity of a binding protein could be altered in a predictable fashion, or that a binding protein of predetermined specificity could be constructed de novo. See, for example, Blackburn (2000) Curr. Opin. Struct. Biol. 10:399-400; Segal et al. (2000) Curr. Opin. Chem. Biol. 4:34-39. To this end, attempts have been made to modify C2H2 zinc finger proteins. See, e.g., U.S. Pat. Nos. 6,007,988; 6,013,453; 6,140,081; PCT WO98/53057; PCT WO98/53058; PCT WO98/53059; PCT WO98/53060; PCT WO00/23464; PCT WO 00/42219; Choo et al. (2000) Curr. Opin. Struct. Biol. 10:411-416; Segal et al. (2000) Curr. Opin. Chem. Biol. 4:34-39; and references cited in these publications.

To date, however, cellular studies using designed C2H2 ZFPs have utilized relatively few positions in the zinc finger as adjustable parameters to obtain optimal activity. In particular, studies to date have modified only those residues at the finger—DNA interface. These have included positions known to make direct base contacts, 'supporting' or 'buttressing' residues immediately adjacent to the base-contacting positions, and positions capable of contacting the phosphate backbone of the DNA. Furthermore, many observed effects have been quite modest, and the possibility that improved ZFP activities might be achieved via substitution of residues at other positions in the finger or using non-C2H2 polypeptides has remained completely uninvestigated.

Thus, there exists a need for additional designed or selected zinc finger binding proteins.

SUMMARY

Disclosed herein are binding proteins, particular zinc finger binding proteins, with modified metal co-ordination sites. Methods of making and using these proteins are also provided. In preferred embodiments, the binding proteins contain three zinc coordinating fingers and one or more of these fingers are modified, non-canonical (e.g., non-C2H2) finger components. Preferably, the third finger of a three-finger ZFP is modified and non-canonical.

In one aspect, an isolated, non-canonical zinc finger binding protein comprising one or more non-canonical zinc finger components that bind to a target sequence is provided. The isolated zinc finger binding protein can be provided as a nucleic acid molecule or as a polypeptide. Furthermore, the target sequence can be an amino acid, DNA (e.g., promoter sequence) or RNA and, additionally, may be in a prokaryotic (e.g., bacteria) or eukaryotic cell (e.g., plant cell, yeast cell, fungal cell, animal such as human). In certain embodiments, the amino acid sequence of one or more of the zinc finger components is X3-B-X2-4-Cys-X12-His-X1-7-His-X4; X3-Cys-X2-4-B-X12-His-X1-7-His-X4; X3-Cys-X2-4-Cys-X12-Z-X1-7-His-X4; X3-Cys-X2-4-Cys-X 12-His-X1-7-Z-X4; X3-B-X2-4-B-X12-His-X1-7-His-X4; X3-B-X2-4-Cys-X12-Z-X1-7-His-X4; X3-B-X2-4-Cys-X12-His-X1-7-Z-X4; X3-Cys-X2-4-B-X12-Z-X1-7-His-X4; X3-Cys-X2-4-B-X12-His-X1-7-Z-X4; X3-Cys-X2-4-Cys-X12-Z-X1-7-Z-X4; X3-Cys-X2-4-B-X12-Z-X1-7-Z-X4; X3-B-X2-4-Cys-X12-Z-X1-7-Z-X4; X3-B-X2-4-B-X12-His-X1-7-Z-X4; X3-B-X2-4-B-X12-Z-X1-7-His-X4; and X3-B-X2-4-B-X12-Z-X1-7-Z-X4, (SEQ ID NOS:118-132, respectively) wherein X is any amino acid, B is any amino acid except cysteine and Z is any amino acid except histidine.

The modified zinc finger proteins described herein can include any number of zinc coordinating finger components in which one or more of the zinc finger coordinates are non-canonical. In preferred embodiments, the ZFP comprises three fingers, wherein one or more of the finger components is non-canonical. In certain embodiments, the third zinc finger component is non-canonical. In other embodiments, any of the ZFPs described herein comprise a modified plant ZFP backbone.

In other aspects, fusion polypeptides comprising (a) any of the zinc finger binding proteins described herein and (b) at least one functional domain are provided. The functional domain may be, for example a repressive domain such as KRAB, MBD-2B, v-ErbA, MBD3, TR, and members of the DNMT family; an activation domain such as VP16, p65 subunit of NF-kappa B, and VP64; an insulator domain; a chromatin remodeling protein; and/or a methyl binding domain.

In other aspects, polynucleotides encoding any of the zinc finger proteins (or fusion molecules) described herein are provided. Expression vectors and host cells comprising these polynucleotides are also provided.

In yet other aspects, a method of modulating expression of a gene is provided. The method comprises the step of contacting a region of DNA with any of the zinc finger containing fusion molecules described herein. In certain embodiments, the zinc finger binding protein of the fusion molecule binds to a target site in a gene encoding a product selected from the group consisting of vascular endothelial growth factor, erythropoietin, androgen receptor, PPAR-γ2, p16, p53, pRb, dystrophin and e-cadherin, delta-9 desaturase, delta-12 desaturases from other plants, delta-15 desaturase, acetyl-CoA carboxylase, acyl-ACP-thioesterase, ADP-glucose pyrophosphorylase, starchsynthase, cellulose synthase, sucrose synthase, senescence-associated genes, heavy metalchelators, fatty acid hydroperoxide lyase, polygalacturonase, EPSP synthase, plant viral genes, plant fungal pathogen genes, and plant bacterial pathogen genes. (See, also WO 00/41566). The gene may in any cell, for example a plant cell or animal (e.g., human) cell.

In still further aspects, compositions comprising any of the zinc finger proteins (or fusion) molecules described herein and a pharmaceutically acceptable excipient are provided.

These and other embodiments will readily occur to those of skill in the art in light of the disclosure herein.

DETAILED DESCRIPTION

General

Figure 1:
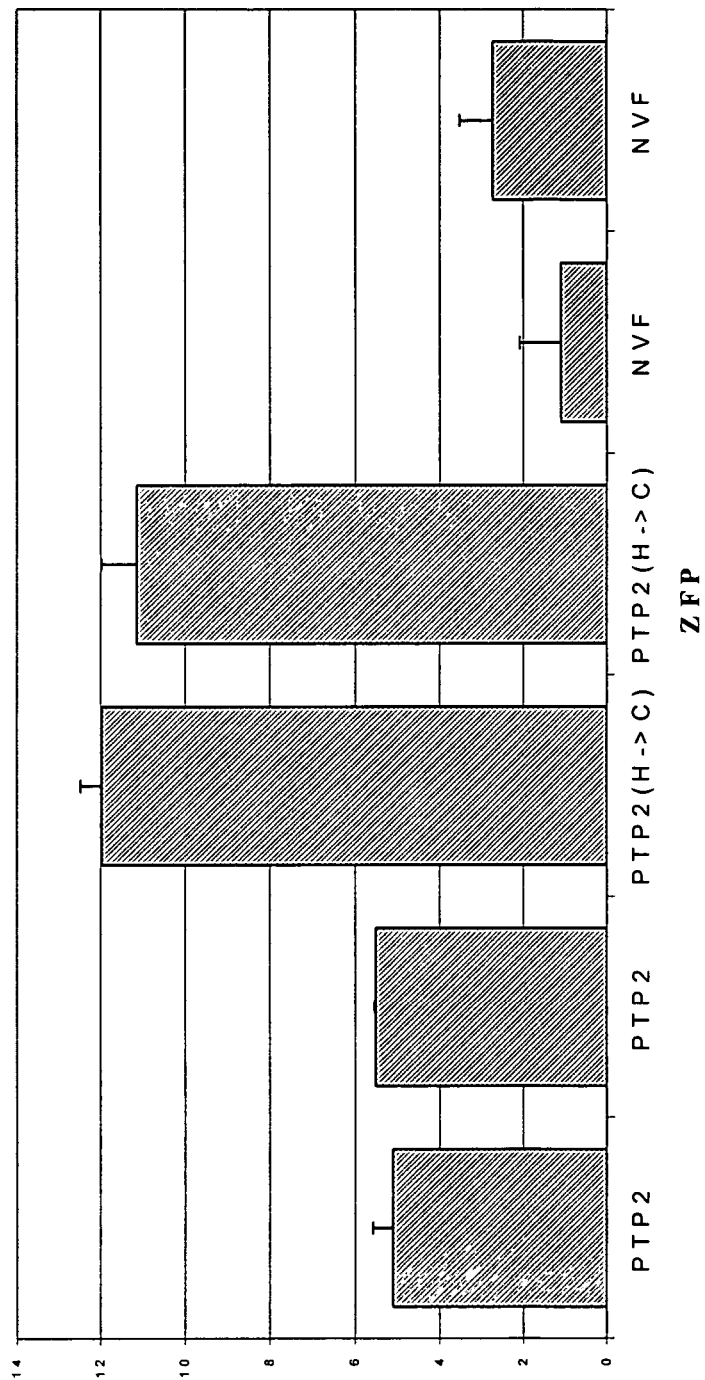
FIG. 1 is a graph depicting levels of LCK gene mRNA (normalized to 18S rRNA levels) in cells transfected with constructs encoding fusions of the VP16 activation domain with a canonical ZFP (PTP2), a modified ZFP (PTP2(H→C), and a control construct (NVF).

The present disclosure provides isolated, non-canonical zinc finger binding polypeptides (ZFPs), wherein one or more of the zinc finger components differs from the canonical consensus sequence of Cys-Cys-His-His (e.g., Cys2-His2). The polypeptide can be a fusion polypeptide and, either by itself or as part of such a fusion, can enhance or suppress transcription of a gene, and may bind to DNA, RNA and/or protein. Polynucleotides encoding non-canonical ZFPs and fusion proteins comprising one or more non-canonical ZFPs are also provided. Additionally provided are pharmaceutical compositions comprising a therapeutically effective amount of any of the modified zinc finger-nucleotide binding polypeptides described herein or functional fragments thereof; or a therapeutically effective amount of a nucleotide sequence that encodes any of the modified zinc finger-nucleotide binding polypeptides or functional fragments thereof, wherein the zinc finger polypeptide or functional fragment thereof binds to a cellular nucleotide sequence to modulate the function of the cellular nucleotide sequence, in combination with a pharmaceutically acceptable carrier. Also provided are screening methods for obtaining a modified zinc finger-nucleotide binding polypeptide which binds to a cellular or viral nucleotide sequence.

Currently, designed and/or selected ZFPs utilize relatively few positions in the zinc finger as adjustable parameters to obtain optimal activity. In particular, studies to date have altered only those residues at the finger—DNA interface. See, e.g., U.S. Pat. Nos. 6,007,988; 6,013,453; 6,140,081 and 6,140,466, as well as PCT WO 00/42219. As noted above, the observed effects have been quite modest, and the possibility that improved ZFP activities might be accessible via substitution of residues at other positions in the finger has not been investigated.

Accordingly, in one embodiment, modified (e.g., non-canonical) zinc finger proteins are described in which the sequence of one or more zinc fingers of the ZFP differs from the canonical consensus sequence containing two cysteine (Cys) residues and two histidine (His) residues:

X$_3$-Cys-X$_{2-4}$-Cys-X$_{12}$-His-X$_{1-7}$-His-X$_4$ (SEQ ID NO: 2)

(also known as the "Cys2-His2" or "C2H2" consensus sequence). As zinc coordination provides the principal folding energy for zinc fingers, adjustment of zinc coordinating residues would appear to provide a ready means for modifying finger stability and structure, which could impact on a variety of important functional features of zinc finger protein—transcription factors. In particular, features such as cellular half-life, interactions with other cellular factors, DNA binding specificity and affinity, and relative orientation of functional domains would all be expected to be influenced by residue choice at the zinc-coordinating positions.

Thus, in preferred embodiments, one or more zinc coordinating fingers making up the zinc finger protein has any of the following sequences:

X3-B-X2-4-Cys-X12-His-X1-7-His-X4 (SEQ ID NO: 118)

X3-Cys-X2-4-B-X12-His-X1-7-His-X4 (SEQ ID NO: 119)

X3-Cys-X2-4-Cys-X12-Z-X1-7-His-X4 (SEQ ID NO: 120)

X3-Cys-X2-4-Cys-X12-His-X1-7-Z-X4 (SEQ ID NO: 121)

X3-B-X2-4-B-X12-His-X1-7-His-X4 (SEQ ID NO: 122)

X3-B-X2-4-Cys-X12-Z-X1-7-His-X4 (SEQ ID NO: 123)

X3-B-X2-4-Cys-X12-His-X1-7-Z-X4 (SEQ ID NO: 124)

X3-Cys-X2-4-B-X12-Z-X1-7-His-X4 (SEQ ID NO: 125)

X3-Cys-X2-4-B-X12-His-X1-7-Z-X4 (SEQ ID NO: 126)

X3-Cys-X2-4-Cys-X12-Z-X1-7-Z-X4 (SEQ ID NO: 127)

X3-Cys-X2-4-B-X12-Z-X1-7-Z-X4 (SEQ ID NO: 128)

X3-B-X2-4-Cys-X12-Z-X1-7-Z-X4 (SEQ ID NO: 129)

X3-B-X2-4-B-X12-His-X1-7-Z-X4 (SEQ ID NO: 130)

X3-B-X2-4-B-X12-Z-X1-7-His-X4 (SEQ ID NO: 131)

X3-B-X2-4-B-X12-Z-X1-7-Z-X4 (SEQ ID NO: 132)

where X=any amino acid
B=any amino acid except cysteine
Z=any amino acid except histidine Additionally, it is preferred that a zinc finger protein comprises at least three zinc coordinating fingers and that at least one of these fingers is non-canonical. In the standard nomenclature for ZFPs, the "first" finger is the N-terminal-most finger of the protein (with respect to the other fingers) and binds to the 3'-most triplet (or quadruplet) subsite in the target site. Additional fingers, moving towards the C-terminus of the protein, are numbered sequentially. For example, in certain embodiments, a three-finger zinc finger protein is provided wherein the first two fingers are of the C2-H2 class but the first or second histidine residue in the third finger (and optionally adjacent amino acid residues) is substituted with Cys or with Cys and additional amino acids, such as glycine. In other embodiments, a three-finger zinc finger protein is provided wherein the first or second cysteine residue in the first finger is substituted with histidine or with histidine and additional amino acids such as glycine. Furthermore, in certain embodiments, a finger of a zinc finger protein is modified such that, in one or more of the fingers, one or more cysteine or histidine residues is replaced with a different amino acid such as, for example, serine. In one embodiment, the second finger of a three-finger zinc finger protein is modified such that one or both of the cysteine residues are replaced with serine (and/or additional amino acids). Additionally, carboxyl-containing amino acids, such as, for example, aspartic acid and glutamic acid are substituted for cysteine and/or histidine in a zinc finger. Furthermore, ZFPs comprising two or more fingers in which more than one finger is modified are also provided.

Therefore, the ZFPs disclosed herein differ from previously described designed zinc finger protein transcription factors in that they comprise at least one zinc-coordinating finger that differs from the canonical consensus sequence (Cys-Cys-His-His). It will be readily apparent that various combinations of modified zinc fingers can be used in a single protein; for example, all of the finger components may be modified using the same or different modified zinc fingers. Alternatively, less than all of the fingers can be modified using the same or different modified fingers. Furthermore, the non-canonical modified finger components described herein can also be used in combination with previously described C2H2 ZFP finger components.

In additional embodiments, the isolated non-canonical zinc fingers described herein are used in fusion proteins, for example fusions of a ZFP DNA-binding domain with repression or activation domains or with chromatin remodeling domains. Polynucleotides encoding any of the zinc finger proteins, components thereof and fusions thereof are also provided.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

Definitions

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally occurring amino acid, for example selenocysteine (Bock et al. (1991) *Trends Biochem. Sci.* 16:463-467; Nasim et al. (2000) *J. Biol. Chem.* 275:14, 846-14,852) and the like.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. A "binding profile" refers to a plurality of target sequences that are recognized and bound by a particular binding protein. For example, a binding profile can be determined by contacting a binding protein with a population of randomized target sequences to identify a sub-population of target sequences bound by that particular binding protein.

A "zinc finger binding protein" is a protein or segment within a larger protein that binds DNA, RNA and/or protein in a sequence-specific manner as a result of stabilization of protein structure through coordination of a zinc ion. The term zinc finger binding protein is often abbreviated as zinc finger protein or ZFP. A "canonical" zinc finger refers to a zinc-coordinating component (e.g., zinc finger) of a zinc finger protein having the general amino acid sequence: $X_3$-Cys-$X_{2-4}$-Cys-$X_{12}$-His-$X_{1-7}$-His-$X_4$ (SEQ ID NO. 2) where X is any amino acid (also known as a C2H2 zinc finger).

A "modified" zinc finger protein is a protein not occurring in nature that has been designed and/or selected so as to comprise a substitution of at least one amino acid, compared to a naturally occurring zinc finger protein. Further, a "designed" zinc finger protein is a protein not occurring in nature whose structure and composition results principally from rational criteria. Rational criteria for design include application of substitution rules and computerized algorithms for processing information in a database storing information of existing ZFP designs and binding data, for example as described in co-owned PCT WO 00/42219. A "selected" zinc finger protein is a protein not found in nature whose production results primarily from an empirical process such as phage display. See e.g., U.S. Pat. No. 5,789,538; U.S. Pat. No. 6,007,988; U.S. Pat. No. 6,013,453; WO 95/19431; WO 96/06166 and WO 98/54311. Designed and/or selected ZFPs are also referred to as "engineered" ZFPs and can be modified according to the methods and compositions disclosed herein (e.g., by conversion to C3H and/or to comprise a plant backbone).

The term "naturally-occurring" is used to describe an object that can be found in nature, as distinct from being artificially produced by a human.

A zinc finger "backbone" is the portion of a zinc finger outside the region involved in DNA major groove interactions; i.e., the regions of the zinc finger outside of residues −1 through +6 of the alpha helix. The backbone comprises the beta strands, the connecting region between the second beta strand and the alpha helix, the portion of the alpha helix distal to the first conserved histidine residue, and the inter-finger linker sequence(s).

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion-polypeptide, the ZFP DNA-binding domain portion is able to bind its target site and/or its binding site, while the transcriptional activation domain (or functional fragment thereof) is able to activate transcription.

"Specific binding" between, for example, a ZFP and a specific target site means a binding affinity of at least $1 \times 10^6$ $M^{-1}$.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see below), as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus. For example, the long terminal repeat (LTR) of retroviruses is a promoter region that may be a target for a modified zinc finger binding polypeptide. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a modified zinc finger binding polypeptide as described herein.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of an mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the modified zinc finger-nucleotide binding polypeptides disclosed herein may modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) *Nature Biotechnology* 15:961-964); changes in signal transduction; changes in phosphorylation and dephosphorylation; changes in receptor-ligand interactions; changes in concentrations of second messengers such as, for example, cGMP, cAMP, IP$_3$, and Ca2$^+$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate (IP$_3$); changes in intracellular calcium levels; cytokine release, and the like.

"Eucaryotic cells" include, but are not limited to, fungal cells (such as yeast), plant cells, animal cells, mammalian cells and human cells. Similarly, "prokaryotic cells' include, but are not limited to, bacteria.

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a ZFP to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340: 245-246; U.S. Pat. No. 5,585,245 and PCT WO 98/44350.

A "target site" or "target sequence" is a sequence that is bound by a binding protein such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

The term "effective amount" includes that amount which results in the desired result, for example, deactivation of a previously activated gene, activation of a previously repressed gene, or inhibition of transcription of a structural gene or translation of RNA.

Zinc Finger Proteins

Zinc finger proteins are formed from zinc finger components. For example, zinc finger proteins can have one to thirty-seven fingers, commonly having 2, 3, 4, 5 or 6 fingers. Zinc finger DNA-binding proteins are described, for example, in Miller et al. (1985) *EMBO J.* 4:1609-1614; Rhodes et al. (1993) *Scientific American* February:56-65; and Klug (1999) *J. Mol. Biol.* 293:215-218. A zinc finger protein recognizes and binds to a target site (sometimes referred to as a target segment) that represents a relatively small subsequence within a target gene. Each component finger of a zinc finger protein binds to a subsite within the target site. The subsite includes a triplet of three contiguous bases on the same strand (sometimes referred to as the target strand). The three bases in the subsite can be individually denoted the 5' base, the mid base, and the 3' base of the triplet, respectively. The subsite may or may not also include a fourth base on the non-target strand that is the complement of the base immediately 3' of the three contiguous bases on the target strand. The base immediately 3' of the three contiguous bases on the target strand is sometimes referred to as the 3' of the 3' base. Alternatively, the four bases of the target strand in a four base subsite can be numbered 4, 3, 2, and 1, respectively, starting from the 5' base.

In discussing the specificity-determining regions of a zinc finger, amino acid +1 refers to the first amino acid in the α-helical portion of the zinc finger. The portion of a zinc finger that is generally believed to be responsible for its binding specificity lies between −1 and +6. Amino acid ++2 refers to the amino acid at position +2 in a second zinc finger adjacent (in the C-terminal direction) to the zinc finger under consideration. In certain circumstances, a zinc finger binds to its triplet subsite substantially independently of other fingers in the same zinc finger protein. Accordingly, the binding specificity of a zinc finger protein containing multiple fingers is, to a first approximation, the aggregate of the specificities of its component fingers. For example, if a zinc finger protein is formed from first, second and third fingers that individually bind to triplets XXX, YYY, and ZZZ, the binding specificity of the zinc finger protein is 3'-XXX YYY ZZZ-5'.

The relative order of fingers in a zinc finger protein, from N-terminal to C-terminal, determines the relative order of triplets in the target sequence, in the 3' to 5' direction that will be recognized by the fingers. For example, if a zinc finger protein comprises, from N-terminal to C-terminal, first, second and third fingers that individually bind to the triplets 5'-GAC-3',5'-GTA-3' and 5'-GGC-3', respectively, then the zinc finger protein binds to the target sequence 5'-GGCGTA-GAC-3' (SEQ ID NO: 3). If the zinc finger protein comprises the fingers in another order, for example, second finger, first finger, third finger, then the zinc finger protein binds to a target segment comprising a different permutation of triplets, in this example, 5'-GGCGACGTA-3' (SEQ ID NO: 4). See Berg et al. (1996) *Science* 271:1081-1086.

A component finger of a zinc finger protein typically contains approximately 30 amino acids and comprises the following canonical consensus sequence (from N to C):

(SEQ ID NO: 1)
Cys-(X)2-4-Cys-X12-His-(X)3-5-His.

Thus, most C2H2 type zinc fingers contain two invariant cysteine residues in the beta turn and two invariant histidine residues, these four residues being coordinated through a zinc atom to maintain the characteristic zinc finger structure. See, e.g., Berg & Shi (1996) *Science* 271:1081-1085. The numbering convention used above is standard in the field for the region of a zinc finger conferring binding specificity. The amino acid on the N-terminal side of the first invariant His residue is assigned the number +6, and other amino acids, proceeding in an N-terminal direction, are assigned successively decreasing numbers. The alpha helix begins at residue +1 and extends to the residue following the second conserved histidine. The entire helix is therefore of variable length, between 11 and 13 residues.

Certain DNA-binding domains are capable of binding to DNA that is packaged in nucleosomes. See, for example, Cordingley et al. (1987) *Cell* 48:261-270; Pina et al. (1990) *Cell* 60:719-731; and Cirillo et al. (1998) *EMBO J.* 17:244-254. Certain ZFP-containing proteins such as, for example, members of the nuclear hormone receptor superfamily, are capable of binding DNA sequences packaged into chromatin. These include, but are not limited to, the glucocorticoid receptor and the thyroid hormone receptor. Archer et al. (1992) *Science* 255:1573-1576; Wong et al. (1997) *EMBO J.* 16:7130-7145. Other DNA-binding domains, including certain ZFP-containing binding domains, require more accessible DNA for binding. In the latter case, the required binding specificity of the DNA-binding domain can be determined by identifying accessible regions in the cellular chromatin. Accessible regions can be determined as described in co-owned International Publications WO 01/83751 and WO 01/83732, the disclosures of which are hereby incorporated by reference herein. A modified ZFP DNA-binding domain is designed and/or selected to bind to a target site within the accessible region.

A. Non-Canonical ZFPs

The compositions and methods disclosed herein include modified, preferably non-canonical (e.g., non-C2H2), zinc finger proteins that specifically bind to a target sequence. Non-canonical ZFP DNA-binding domains can be designed and/or selected to recognize a particular target site, for example as described in co-owned WO 00/42219; WO 00/41566; as well as U.S. Pat. Nos. 5,789,538; 6,007,408; 6,013,453; 6,140,081 and 6,140,466; and PCT publications WO 95/19431, WO 98/54311, WO 00/23464 and WO 00/27878. In preferred embodiments, the process of designing or selecting a non-canonical, non-naturally occurring ZFP typically starts with a natural ZFP as a source of framework residues, as described in co-owned PCT WO 00/42219; WO 98/53057; WO 98/53058; WO 98/53059 and WO 98/53060.

Briefly, the methods disclosed herein serve to modify the typically invariant Cys and His residues while maintaining (or enhancing) the desired binding specificity of a ZFP. The process of obtaining a non-naturally occurring ZFP with a predetermined binding specificity typically starts with a natural ZFP as a source of framework residues. The process of design or selection serves to define non-conserved positions (i.e., positions −1 to +6) so as to confer a desired binding specificity. One ZFP suitable for use as a framework is the DNA-binding domain of the mouse transcription factor Zif268. Another suitable natural zinc finger protein as a source of framework residues is Sp-1. The Sp-1 sequence used for construction of zinc finger proteins corresponds to amino acids 531 to 624 in the Sp-1 transcription factor. An additional useful ZFP backbone is that of the Sp-1 consensus sequence, described by Shi et al. (1995) *Chemistry and Biology* 1:83-89. The amino acid sequences of these ZFP frameworks are disclosed in co-owned PCT WO 00/42219, the disclosure of which is incorporated by reference. In other aspects, the ZFP backbone will comprise a modified plant ZFP backbone into which one or more of the non-canonical fingers described herein are inserted so that they bind to a target sequence. Other suitable ZFPs are known to those of skill in the art and are described herein. The documents cited supra also disclose methods of assessing binding specificity of modified ZFPs.

Non-canonical zinc fingers therefore include one or more zinc finger components in which at least one of the C2H2 amino acids has been replaced with one or more amino acids. In certain embodiments, more than one of the canonical amino acids is replaced. Examples of non-canonical zinc finger components include:

X3-B-X2-4-Cys-X12-His-X1-7-His-X4 (SEQ ID NO: 118)

X3-Cys-X2-4-B-X12-His-X1-7-His-X4 (SEQ ID NO: 119)

X3-Cys-X2-4-Cys-X12-Z-X1-7-His-X4 (SEQ ID NO: 120)

X3-Cys-X2-4-Cys-X12-His-X1-7-Z-X4 (SEQ ID NO: 121)

X3-B-X2-4-B-X12-His-X1-7-His-X4 (SEQ ID NO: 122)

X3-B-X2-4-Cys-X12-Z-X1-7-His-X4 (SEQ ID NO: 123)

X3-B-X2-4-Cys-X12-His-X1-7-Z-X4 (SEQ ID NO: 124)

X3-Cys-X2-4-B-X12-Z-X1-7-His-X4 (SEQ ID NO: 125)

X3-Cys-X2-4-B-X12-His-X1-7-Z-X4 (SEQ ID NO: 126)

X3-Cys-X2-4-Cys-X12-Z-X1-7-Z-X4 (SEQ ID NO: 127)

X3-Cys-X2-4-B-X12-Z-X1-7-Z-X4 (SEQ ID NO: 128)

X3-B-X2-4-Cys-X12-Z-X1-7-Z-X4 (SEQ ID NO: 129)

X3-B-X2-4-B-X12-His-X1-7-Z-X4 (SEQ ID NO: 130)

X3-B-X2-4-B-X12-Z-X1-7-His-X4 (SEQ ID NO: 131)

X3-B-X2-4-B-X12-Z-X1-7-Z-X4 (SEQ ID NO: 132)

X3-Y-X2-4-Cys-X12-His-X1-7-His-X4 (SEQ ID NO: 133)

X3-Cys-X2-4-Y-X12-His-X1-7-His-X4 (SEQ ID NO: 134)

X3-Cys-X2-4-Cys-X12-Y-X1-7-His-X4 (SEQ ID NO: 135)

X3-Cys-X2-4-Cys-X12-His-X1-7-Y-X4 (SEQ ID NO: 136)

X3-Y-X2-4-Y-X12-His-X1-7-His-X4 (SEQ ID NO: 137)

X3-Y-X2-4-Cys-X12-Y-X1-7-His-X4 (SEQ ID NO: 138)

X3-Y-X2-4-Cys-X12-His-X1-7-Y-X4 (SEQ ID NO: 139)

X3-Cys-X2-4-Y-X12-Y-X1-7-His-X4 (SEQ ID NO: 140)

X3-Cys-X2-4-Y-X12-His-X1-7-Y-X4 (SEQ ID NO: 141)

X3-Cys-X2-4-Cys-X12-Y-X1-7-Y-X4 (SEQ ID NO: 142)

X3-Cys-X2-4-Y-X12-Y-X1-7-Y-X4 (SEQ ID NO: 143)

X3-Y-X2-4-Cys-X12-Y-X1-7-Y-X4 (SEQ ID NO: 144)

X3-Y-X2-4-Y-X12-His-X1-7-Y-X4 (SEQ ID NO: 145)

X3-Y-X2-4-Y-X12-Y-X1-7-His-X4 (SEQ ID NO: 146)

X3-Y-X2-4-Y-X12-Y-X1-7-Y-X4 (SEQ ID NO: 147)

where X=any amino acid
  B=any amino acid except cysteine
  Z=any amino acid except histidine
  Y=any amino acid except histidine or cysteine A modified ZFP can include any number of zinc finger components, although a three-finger structure is generally preferred. Typically, the C-terminal-most (e.g., third) finger of the ZFP is modified and non-canonical. The other fingers of the protein may be naturally occurring zinc finger components, non-canonical modified components, modified C2H2 fingers or combinations of these components. Thus, as described below in Example 2, in certain embodiments, a three-finger zinc finger binding protein is provided wherein the first two fingers are of the C2-H2 class and, in the third (C-terminal-most) finger, the second histidine is substituted with Cys or with Cys and additional amino acids, such as glycine. In other embodiments, a three-finger zinc finger protein is provided wherein, in the first (N-terminal-most) finger, the first cysteine residue is substituted with histidine or with histidine and additional amino acids such as glycine. Furthermore, in certain embodiments, the second (middle) finger of a three-finger ZFP is modified such that one or both of the cysteines are replaced with serines (and/or additional amino acids).

Also included herein are nucleic acids encoding a ZFP comprising at least one non-canonical zinc finger as described herein.

B. Linkage

Two or more zinc finger proteins can be linked to have a target site specificity that is, to a first approximation, the aggregate of that of the component zinc finger proteins. For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 5'-CCCBB-BAAANZZZYYYXXX-3', where N indicates a short intervening region (typically 0-5 bases of any type). In this situation, the target site can be viewed as comprising two target segments separated by an intervening segment.

Linkage of zinc finger proteins can be accomplished using any of the following peptide linkers:

TGEKP  Liu et al. (1997) Proc. Natl. Acad. Sci. USA 94: 5525-5530. (SEQ ID NO: 5)

(G4S)n  Kim et al. (1996) Proc. Natl. Acad. Sci. USA 93:1156-1160. (SEQ ID NO: 6)

GGRRGGGS (SEQ ID NO: 7)

LRQRDGERP (SEQ ID NO: 8)

LRQKDGGGSERP (SEQ ID NO: 9)

LRQKD(G3S)2ERP. (SEQ ID NO: 10)

Alternatively, flexible linkers can be rationally designed using computer programs capable of modeling both DNA-binding sites and the peptides themselves, or by phage display methods. In a further variation, non-covalent linkage can be achieved by fusing two zinc finger proteins with domains promoting heterodimer formation of the two zinc finger proteins. For example, one zinc finger protein can be fused with fos and the other with jun (see Barbas et al., WO 95/119431). Alternatively, dimerization interfaces can be obtained by selection. See, for example, Wang et al. (1999) Proc. Natl. Acad. Sci. USA 96:9568-9573.

Linkage of two or more zinc finger proteins is advantageous for conferring a unique binding specificity within a mammalian genome. A typical mammalian diploid genome consists of $3 \times 10^9$ bp. Assuming that the four nucleotides A, C, G, and T are randomly distributed, a given 9 bp sequence is present ~23,000 times. Thus a three-finger ZFP recognizing a 9 bp target with absolute specificity would have the potential to bind to ~23,000 sites within the genome. An 18 bp sequence is present once in $3.4 \times 10^{10}$ bp, or about once in a random DNA sequence whose complexity is ten times that of a mammalian genome. Thus, linkage of two three-finger ZFPs, to recognize an 18 bp target sequence, provides the requisite specificity to target a unique site in a typical mammalian genome.

C. Fusion Molecules

The selection and/or design of non-canonical zinc finger-containing proteins also allows for the design of fusion molecules that facilitate regulation of gene expression. Thus, in certain embodiments, the compositions and methods disclosed herein involve fusions between at least one of the zinc finger proteins described herein (or functional fragments thereof) and one or more functional domains (or functional fragments thereof), or a polynucleotide encoding such a fusion. The presence of such a fusion molecule in a cell allows a functional domain to be brought into proximity with a sequence in a gene that is bound by the zinc finger portion of the fusion molecule. The transcriptional regulatory function of the functional domain is then able to act on the gene, by, for example, modulating expression of the gene.

In certain embodiments, fusion proteins comprising a modified zinc finger DNA-binding domain and a functional domain are used for modulation of endogenous gene expression as described, for example, in co-owned PCT WO 00/41566. Modulation includes repression and activation of gene expression; the nature of the modulation generally depending on the type of functional domain present in the fusion protein. Any polypeptide sequence or domain capable of influencing gene expression (or functional fragment thereof) that can be fused to a DNA-binding domain, is suitable for use.

An exemplary functional domain for fusing with a ZFP DNA-binding domain, to be used for repressing gene expression, is a KRAB repression domain from the human KOX-1 protein (see, e.g., Thiesen et al., New Biologist 2, 363-374

(1990); Margolin et al., *Proc. Natl. Acad. Sci. USA* 91, 4509-4513 (1994); Pengue et al., *Nucl. Acids Res.* 22:2908-2914 (1994); Witzgall et al., *Proc. Natl. Acad. Sci. USA* 91, 4514-4518 (1994). Another suitable repression domain is methyl binding domain protein 2B (MBD-2B) (see, also Hendrich et al. (1999) *Mamm Genome* 10:906-912 for description of MBD proteins). Another useful repression domain is that associated with the v-ErbA protein. See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenke et al. (1988) *Cell* 52:107-119; and Zenke et al. (1990) *Cell* 61:1035-1049. Additional exemplary repression domains include, but are not limited to, thyroid hormone receptor (TR), SID, MBD1, MBD2, MBD3, MBD4, MBD-like proteins, members of the DNMT family (e.g., DNMT1, DNMT3A, DNMT3B), Rb, MeCP1 and MeCP2. See, for example, Zhang et al. (2000) *Ann Rev Physiol* 62:439-466; Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chern et al. (1996) *Plant Cell* 8:305-321; and Wu et al. (2000) *Plant J.* 22:19-27.

Suitable domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Additional exemplary activation domains include, but are not limited to, p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Additional functional domains are disclosed, for example, in co-owned WO 00/41566. Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13-22 (1994), and methyltransferases are described in Cheng, *Curr. Opin. Struct. Biol.* 5:4-10 (1995). Chromatin associated proteins and their modifiers (e.g., kinases, acetylases and deacetylases), such as histone deacetylase (Wolffe, *Science* 272:371-2 (1996)) are also useful as domains for addition to the ZFP of choice. In one preferred embodiment, the regulatory domain is a DNA methyl transferase that acts as a transcriptional repressor (see, e.g., Van den Wyngaert et al., *FEBS Lett.* 426:283-289 (1998); Flynn et al., *J. Mol. Biol.* 279:101-116 (1998); Okano et al., *Nucleic Acids Res.* 26:2536-2540 (1998); and Zardo & Caiafa, *J. Biol. Chem.* 273:16517-16520 (1998)). In another preferred embodiment, endonucleases such as Fok1 are used as transcriptional repressors, which act via gene cleavage (see, e.g., WO95/09233; and PCT/US94/01201). Further, insulator domains, chromatin remodeling proteins such as ISWI-containing domains and/or methyl binding domain proteins suitable for use in fusion molecules are described, for example, in WO 01/83793, WO 02/26959, WO 02/26960 and WO 02/44376.

In additional embodiments, targeted remodeling of chromatin, as disclosed in co-owned International patent publication WO 01/83793 can be used to generate one or more sites in cellular chromatin that are accessible to the binding of a functional domain/modified ZFP fusion molecule.

Fusion molecules are constructed by methods of cloning and biochemical conjugation that are well known to those of skill in the art. Fusion molecules comprise a modified ZFP binding domain and, for example, a transcriptional activation domain, a transcriptional repression domain, a component of a chromatin remodeling complex, an insulator domain or a functional fragment of any of these domains. In certain embodiments, fusion molecules comprise a non-canonical zinc finger protein and at least two functional domains (e.g., an insulator domain or a methyl binding protein domain and, additionally, a transcriptional activation or repression domain). Fusion molecules also optionally comprise nuclear localization signals (such as, for example, that from the SV40 medium T-antigen) and epitope tags (such as, for example, FLAG, see Example 2, and hemagglutinin). Fusion proteins (and nucleic acids encoding them) are designed such that the translational reading frame is preserved among the components of the fusion.

The fusion molecules disclosed herein comprise a non-canonical zinc finger binding protein which binds to a target site. In certain embodiments, the target site is present in an accessible region of cellular chromatin. Accessible regions can be determined as described in co-owned International PCT Publications WO 01/83751 and WO 01/83732. If the target site is not present in an accessible region of cellular chromatin, one or more accessible regions can be generated as described, for example, in co-owned International PCT Publication WO 01/83793.

In additional embodiments, the non-canonical zinc finger component of a fusion molecule is capable of binding to cellular chromatin regardless of whether its target site is in an accessible region or not. For example, a modified ZFP as disclosed herein can be capable of binding to linker DNA and/or to nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

Methods of gene regulation using a functional domain, targeted to a specific sequence by virtue of a fused DNA binding domain, can achieve modulation of gene expression. Genes so modulated can be endogenous genes or exogenous genes. Modulation of gene expression can be in the form of repression (e.g., repressing expression of exogenous genes, for example, when the target gene resides in a pathological infecting microorganism, or repression of an endogenous gene of the subject, such as an oncogene or a viral receptor, that contributes to a disease state). As described herein, repression of a specific target gene can be achieved by using a fusion molecule comprising a non-canonical zinc finger protein and a functional domain.

Alternatively, modulation can be in the form of activation, if activation of a gene (e.g., a tumor suppressor gene or a transgene) can ameliorate a disease state. In this case, cellular chromatin is contacted with any of the fusion molecules described herein, wherein the modified zinc finger portion of the fusion molecule is specific for the target gene. The functional domain (e.g., insulator domain, activation domain, etc.) enables increased and/or sustained expression of the target gene.

For any such applications, the fusion molecule(s) can be formulated with a pharmaceutically acceptable carrier, as is known to those of skill in the art. See, for example, Remington's Pharmaceutical Sciences, $17^{th}$ ed., 1985; and co-owned WO 00/42219.

Polynucleotide and Polypeptide Delivery

The compositions described herein can be provided to the target cell in vitro or in vivo. In addition, the compositions can be provided as polypeptides, polynucleotides or combination thereof.

A. Delivery of Polynucleotides

In certain embodiments, the compositions are provided as one or more polynucleotides. Further, as noted above, a non-canonical zinc finger protein-containing composition can be designed as a fusion between a polypeptide zinc finger and a functional domain that is encoded by a fusion nucleic acid. In both fusion and non-fusion cases, the nucleic acid can be cloned into intermediate vectors for transformation into prokaryotic or eukaryotic cells for replication and/or expression. Intermediate vectors for storage or manipulation of the nucleic acid or production of protein can be prokaryotic vectors, (e.g., plasmids), shuttle vectors, insect vectors, or viral vectors for example. A nucleic acid encoding a non-canonical zinc finger protein can also cloned into an expression vector, for administration to a bacterial cell, fungal cell, protozoal cell, plant cell, or animal cell, preferably a mammalian cell, more preferably a human cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli, Bacillus* sp., and *Salmonella*. Palva et al. (1983) *Gene* 22:229-235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of the nucleic acid of choice depends on the particular application. For example, a strong constitutive promoter is typically used for expression and purification. In contrast, when a protein is to be used in vivo, either a constitutive or an inducible promoter is used, depending on the particular use of the protein. In addition, a weak promoter can be used, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system. See, e.g., Gossen et al. (1992) *Proc. Natl. Acad. Sci USA* 89:5547-5551; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the resulting ZFP polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and sub-cellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with a nucleic acid sequence coding for a ZFP as described herein under the transcriptional control of the polyhedrin promoter or any other strong baculovirus promoter.

Elements that are typically included in expression vectors also include a replicon that functions in *E. coli* (or in the prokaryotic host, if other than *E. coli*), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of non-canonical zinc finger proteins, which can be purified, if desired, using standard techniques. See, e.g., Colley et al. (1989) *J. Biol. Chem.* 264:17619-17622; and *Guide to Protein Purification, in Methods in Enzymology*, vol. 182 (Deutscher, ed.) 1990. Transformation of eukaryotic and prokaryotic cells is performed according to standard techniques. See, e.g., Morrison (1977) *J. Bacteriol.* 132:349-351; Clark-Curtiss et al. (1983) in *Methods in Enzymology* 101:347-362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Conventional viral and non-viral based gene transfer methods can be used to introduce nucleic acids into mammalian cells or target tissues. Such methods can be used to administer nucleic acids encoding reprogramming polypeptides to cells in vitro. Preferably, nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of gene therapy procedures, see, for example, Anderson (1992) *Science* 256:808-813; Nabel et al. (1993) *Trends Biotechnol.* 11:211-217; Mitani et al. (1993) *Trends Biotechnol.* 11:162-166; Dillon (1993) *Trends Biotechnol.* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer et al. (1995) *British Medical Bulletin* 51(1):31-44; Haddada et al., in *Current Topics in Microbiology and Immunology*, Doerfler and Böhm (eds), 1995; and Yu et al. (1994) *Gene Therapy* 1:13-26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Nucleic acid can be delivered to cells (ex vivo administration) or to target tissues (in vivo administration).

The preparation of lipid:nucleic acid complexes, including targeted liposomes such as immunolipid complexes, is well known to those of skill in the art. See, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, wherein the modified cells are administered to patients (ex vivo). Conventional viral based systems for the delivery of ZFPs include retroviral, lentiviral, poxviral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral gene transfer system would therefore depend on the target tissue. Retroviral vectors have a packaging capacity of up to 6-10 kb of foreign sequence and are comprised of cis-acting long terminal repeats (LTRs). The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al. (1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; and PCT/US94/05700).

Adeno-associated virus (AAV) vectors are also used to transduce cells with target nucleic acids, e.g., in the in vitro production of nucleic acids and peptides, and for in vivo and ex vivo gene therapy procedures. See, e.g., West et al. (1987) *Virology* 160:38-47; U.S. Pat. No. 4,797,368; WO 93/24641; Kotin (1994) *Hum. Gene Ther.* 5:793-801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin, et al. (1984) *Mol. Cell. Biol.* 4:2072-2081; Hermonat et al. (1984) *Proc. Natl. Acad. Sci. USA* 81:6466-6470; and Samulski et al. (1989) *J. Virol.* 63:3822-3828.

Recombinant adeno-associated virus vectors based on the defective and nonpathogenic parvovirus adeno-associated virus type 2 (AAV-2) are a promising gene delivery system. Exemplary AAV vectors are derived from a plasmid containing the AAV 145 bp inverted terminal repeats flanking a transgene expression cassette. Efficient gene transfer and stable transgene delivery due to integration into the genomes of the transduced cell are key features for this vector system. Wagner et al. (1998) *Lancet* 351(9117):1702-3; and Kearns et al. (1996) *Gene Ther.* 9:748-55.

pLASN and MFG-S are examples are retroviral vectors that have been used in clinical trials. Dunbar et al. (1995) *Blood* 85:3048-305; Kohn et al. (1995) *Nature Med.* 1:1017-102; Malech et al. (1997) *Proc. Natl. Acad. Sci. USA* 94:12133-12138. PA317/pLASN was the first therapeutic vector used in a gene therapy trial. (Blaese et al. (1995) *Science* 270:475-480. Transduction efficiencies of 50% or greater have been observed for MFG-S packaged vectors. Ellem et al. (1997) *Immunol Immunother.* 44(1):10-20; Dranoff et al. (1997) *Hum. Gene Ther.* 1:111-2.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenovirus (Ad) vectors can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al. (1998) *Hum. Gene Ther.* 7:1083-1089. Additional examples of the use of adenovirus vectors for gene transfer in clinical trials include Rosenecker et al. (1996) *Infection* 24:5-10; Sterman et al., supra; Welsh et al. (1995) *Hum. Gene Ther.* 2:205-218; Alvarez et al. (1997) *Hum. Gene Ther.* 5:597-613; and Topf et al. (1998) *Gene Ther.* 5:507-513.

Packaging cells are used to form virus particles that are capable of infecting a host cell. Such cells include 293 cells, which package adenovirus, and Ψ2 cells or PA317 cells, which package retroviruses. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many gene therapy applications, it is desirable that the gene therapy vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described infra. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art. See, e.g., Freshney et al., *Culture of Animal Cells, A Manual of Basic Technique,* 3rd ed., 1994, and references cited therein, for a discussion of isolation and culture of cells from patients.

In one embodiment, hematopoietic stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ stem cells in vitro into clinically important immune cell types using cytokines such a GM-CSF, IFN-γ and TNF-α are known. Inaba et al. (1992) *J. Exp. Med.* 176:1693-1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells). See Inaba et al., supra.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions described herein. See, e.g., *Remington's Pharmaceutical Sciences,* 17th ed., 1989.

B. Delivery of Polypeptides

In additional embodiments, fusion proteins are administered directly to target cells. In certain in vitro situations, the target cells are cultured in a medium containing a fusion protein comprising one or more functional domains fused to one or more of the modified ZFPs described herein.

An important factor in the administration of polypeptide compounds is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, *Antennapedia*, was found to be the third helix of the protein, from amino acid position 43 to 58. Prochiantz (1996) *Curr. Opin. Neurobiol.* 6:629-634. Another subsequence, the h (hydrophobic) domain of signal peptides, was found to have similar cell membrane translocation characteristics. Lin et al. (1995) *J. Biol. Chem.* 270:14255-14258.

Examples of peptide sequences which can be linked to a non-canonical zinc finger polypeptide (or fusion containing the same) for facilitating its uptake into cells include, but are not limited to: an 11 amino acid peptide of the tat protein of HIV; a 20 residue peptide sequence which corresponds to amino acids 84-103 of the p16 protein (see Fahraeus et al. (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223-233). Other suitable chemical moieties that provide enhanced cellular uptake can also be linked, either covalently or non-covalently, to the ZFPs.

Toxin molecules also have the ability to transport polypeptides across cell membranes. Often, such molecules (called "binary toxins") are composed of at least two parts: a translocation or binding domain and a separate toxin domain. Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334-3341; Perelle et al. (1993) *Infect. Immun.* 61:5147-5156; Stenmark et al. (1991) *J. Cell Biol.* 113:1025-1032; Donnelly et al. (1993) *Proc. Natl. Acad. Sci. USA* 90:3530-3534; Carbonetti et al. (1995) *Abstr. Annu. Meet. Am. Soc. Microbiol.* 95:295; Sebo et al. (1995) *Infect. Immun.* 63:3851-3857; Klimpel et al. (1992) *Proc. Natl. Acad. Sci. USA.* 89:10277-10281; and Novak et al. (1992) *J. Biol. Chem.* 267:17186-17193.

Such subsequences can be used to translocate polypeptides, including the polypeptides as disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the compound into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629-634; Fraley, et al. (1979) *Proc. Natl. Acad. Sci. USA* 76:3348-3352; Hope et al. (1985) *Biochim. Biophys. Acta* 812:55-65; Mayer et al. (1986) *Biochim. Biophys. Acta* 858:161-168; Williams et al. (1988) *Proc. Natl. Acad. Sci. USA* 85:242-246; *Liposomes*, Ostro (ed.), 1983, Chapter 1); Hope et al. (1986) *Chem. Phys. Lip.* 40:89; Gregoriadis, *Liposome Technology* (1984) and Lasic, *Liposomes: from Physics to Applications* (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337-16342 and Leonetti et al. (1990) *Proc. Natl. Acad. Sci. USA* 87:2448-2451.

Pharmaceutical Compositions and Administration

The modified zinc finger proteins and fusion molecules as disclosed herein, and expression vectors encoding these polypeptides, can be used in conjunction with various methods of gene therapy to facilitate the action of a therapeutic gene product. In such applications, the ZFP-containing compositions can be administered directly to a patient, e.g., to facilitate the modulation of gene expression and for therapeutic or prophylactic applications, for example, cancer (including tumors associated with Wilms' third tumor gene), ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms whose inhibition can be facilitated through use of the methods and compositions disclosed herein include pathogenic bacteria, e.g., Chlamydia, Rickettsial bacteria, Mycobacteria, Staphylococci, Streptococci, Pneumococci, Meningococci and Conococci, Klebsiella, Proteus, Serratia, Pseudomonas, Legionella, Diphtheria, Salmonella, Bacilli (e.g., anthrax), Vibrio (e.g., cholera), Clostridium (e.g., tetanus, botulism), Yersinia (e.g., plague), Leptospirosis, and Borrellia (e.g., Lyme disease bacteria); infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia*, etc.); viruses, e.g., hepatitis (A, B, or C); herpes viruses (e.g., VZV, HSV-1, HHV-6, HSV-II, CMV, and EBV), HIV, Ebola, Marburg and related hemorrhagic fever-causing viruses, adenoviruses, influenza viruses, flaviviruses, echoviruses, rhinoviruses, coxsackie viruses, cornaviruses, respiratory syncytial viruses, mumps viruses, rotaviruses, measles viruses, rubella viruses, parvoviruses, vaccinia viruses, HTLV viruses, retroviruses, lentiviruses, dengue viruses, papillomaviruses, polioviruses, rabies viruses, and arboviral encephalitis viruses, etc.

Administration of therapeutically effective amounts of modified ZFPs described herein, fusion molecules including these ZFPs, or nucleic acids encoding these polypeptides, is by any of the routes normally used for introducing polypeptides or nucleic acids into ultimate contact with the tissue to be treated. The polypeptides or nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions. See, e.g., *Remington's Pharmaceutical Sciences*, 17th ed. 1985.

ZFPs and ZFP fusion polypeptides or nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind known to those of skill in the art.

Applications

The compositions and methods disclosed herein can be used to facilitate a number of processes involving transcriptional regulation. These processes include, but are not limited to, transcription, replication, recombination, repair, integration, maintenance of telomeres, processes involved in chromosome stability and disjunction, and maintenance and propagation of chromatin structures. Accordingly, the methods and compositions disclosed herein can be used to affect any of these processes, as well as any other process that can be influenced by ZFPs or ZFP fusions.

In preferred embodiments, one or more of the molecules described herein are used to achieve targeted activation or repression of gene expression, e.g., based upon the specificity of the modified ZFP. In another embodiment, one or more of the molecules described herein are used to achieve reactivation of a gene, for example a developmentally silenced gene; or to achieve sustained activation of a transgene. The modified ZFP can be targeted to a region outside of the coding region of the gene of interest and, in certain embodiments, is targeted to a region outside the regulatory region(s) of the gene. In these embodiments, additional molecules, exogenous and/or endogenous, can be used to facilitate repression or activation of gene expression. The additional molecules can also be fusion molecules, for example, fusions between a ZFP and a functional domain such as an activation or repression domain. See, for example, co-owned WO 00/41566.

Accordingly, expression of any gene in any organism can be modulated using the methods and compositions disclosed herein, including therapeutically relevant genes, genes of infecting microorganisms, viral genes, and genes whose expression is modulated in the processes of drug discovery and/or target validation. Such genes include, but are not limited to, Wilms' third tumor gene (WT3), vascular endothelial growth factors (VEGFs), VEGF receptors (e.g., flt and flk) CCR-5, low density lipoprotein receptor (LDLR), estrogen receptor, HER-2/neu, BRCA-1, BRCA-2, phosphoenolpyruvate carboxykinase (PEPCK), CYP7, fibrinogen, apolipoprotein A (ApoA), apolipoprotein B (ApoB), renin, phosphoenolpyruvate carboxykinase (PEPCK), CYP7, fibrinogen, nuclear factor κB (NF-κB), inhibitor of NF-κB (I-κB), tumor necrosis factors (e.g., TNF-α, TNF-β), interleukin-1 (IL-1), FAS (CD95), FAS ligand (CD95L), atrial natriuretic factor, platelet-derived factor (PDF), amyloid precursor protein (APP), tyrosinase, tyrosine hydroxylase, β-aspartyl hydroxylase, alkaline phosphatase, calpains (e.g., CAPN10) neuronal pentraxin receptor, adriamycin response protein, apolipoprotein E (apoE), leptin, leptin receptor, UCP-1, IL-1, IL-1 receptor, IL-2, IL-3, IL-4, IL-5, IL-6, IL-12, IL-15, interleukin receptors, G-CSF, GM-CSF, colony stimulating factor, erythropoietin (EPO), platelet-derived growth factor (PDGF), PDGF receptor, fibroblast growth factor (FGF), FGF receptor, PAF, p16, p19, p53, Rb, p21, myc, myb, globin, dystrophin, eutrophin, cystic fibrosis transmembrane conductance regulator (CFTR), GNDF, nerve growth factor (NGF), NGF receptor, epidermal growth factor (EGF), EGF receptor, transforming growth factors (e.g., TGF-α, TGF-β), fibroblast growth factor (FGF), interferons (e.g., IFN-α, IFN-β and IFN-γ), insulin-related growth factor-1 (IGF-1), angiostatin, ICAM-1, signal transducer and activator of transcription (STAT), androgen receptors, e-cadherin, cathepsins (e.g., cathepsin W), topoisomerase, telomerase, bcl, bcl-2, Bax, T Cell-specific tyrosine kinase (Lck), p38 mitogen-activated protein kinase, protein tyrosine phosphatase (hPTP), adenylate cyclase, guanylate cyclase, α7 neuronal nicotinic acetylcholine receptor, 5-hydroxytryptamine (serotonin)-2A receptor, transcription elongation factor-3 (TEF-3), phosphatidylcholine transferase, ftz, PTI-1, polygalacturonase, EPSP synthase, FAD2-1, Δ-9 desaturase, Δ-12 desaturase, Δ-15 desaturase, acetyl-Coenzyme A carboxylase, acyl-ACP thioesterase, ADP-glucose pyrophosphorylase, starch synthase, cellulose synthase, sucrose synthase, fatty acid hydroperoxide lyase, and peroxisome proliferator-activated receptors, such as PPAR-γ2.

Expression of human, mammalian, bacterial, fungal, protozoal, Archaeal, plant and viral genes can be modulated; viral genes include, but are not limited to, hepatitis virus genes such as, for example, HBV-C, HBV-S, HBV-X and HBV-P; and HIV genes such as, for example, tat and rev. Modulation of expression of genes encoding antigens of a pathogenic organism can be achieved using the disclosed methods and compositions.

Additional genes include those encoding cytokines, lymphokines, interleukins, growth factors, mitogenic factors, apoptotic factors, cytochromes, chemotactic factors, chemokine receptors (e.g., CCR-2, CCR-3, CCR-5, CXCR-4), phospholipases (e.g., phospholipase C), nuclear receptors, retinoid receptors, organellar receptors, hormones, hormone receptors, oncogenes, tumor suppressors, cyclins, cell cycle checkpoint proteins (e.g., Chk1, Chk2), senescence-associated genes, immunoglobulins, genes encoding heavy metal chelators, protein tyrosine kinases, protein tyrosine phosphatases, tumor necrosis factor receptor-associated factors (e.g., Traf-3, Traf-6), apolipoproteins, thrombic factors, vasoactive factors, neuroreceptors, cell surface receptors, G-proteins, G-protein-coupled receptors (e.g., substance K receptor, angiotensin receptor, α- and β-adrenergic receptors, serotonin receptors, and PAF receptor), muscarinic receptors, acetylcholine receptors, GABA receptors, glutamate receptors, dopamine receptors, adhesion proteins (e.g., CAMs, selectins, integrins and immunoglobulin superfamily members), ion channels, receptor-associated factors, hematopoietic factors, transcription factors, and molecules involved in signal transduction. Expression of disease-related genes, and/ or of one or more genes specific to a particular tissue or cell type such as, for example, brain, muscle, heart, nervous system, circulatory system, reproductive system, genitourinary system, digestive system and respiratory system can also be modulated.

Other applications include therapeutic methods in which a modified ZFP, a ZFP fusion polypeptide, or a nucleic acid encoding a modified ZFP or a ZFP fusion is administered to a subject and used to modulate the expression of a target gene within the subject (as disclosed, for example, in co-owned PCT WO 00/41566). The modulation can be in the form of repression, for example, when the target gene resides in a pathological infecting microorganism, or in an endogenous gene of the patient, such as an oncogene or viral receptor, that is contributing to a disease state. Alternatively, the modulation can be in the form of activation, when activation of expression or increased expression of an endogenous cellular gene (such as, for example, a tumor suppressor gene) can ameliorate a disease state. Exemplary ZFP fusion polypeptides for both activation and repression of gene expression are disclosed supra. For such applications, modified ZFPs, ZFP fusion polypeptides or, more typically, nucleic acids encoding them are formulated with a pharmaceutically acceptable carrier as a pharmaceutical composition.

Pharmaceutically acceptable carriers and excipients are determined in part by the particular composition being administered, as well as by the particular method used to administer the composition. See, for example, *Remington's Pharmaceutical Sciences*, 17$^{th}$ ed., 1985. ZFPs, ZFP fusion polypeptides, or polynucleotides encoding ZFP fusion polypeptides, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a patient should be sufficient to affect a beneficial therapeutic response in the patient over time. The dose is determined by the efficacy and binding affinity ($K_d$) of the particular ZFP employed, the target cell, and the condition of the patient, as well as the body weight or surface area of the patient to be treated. The size of the dose also is determined by the existence, nature, and extent of any adverse side effects that accompany the administration of a particular compound or vector in a particular patient.

In other applications, modified ZFPs and other DNA- and/ or RNA-binding proteins are used in diagnostic methods for sequence-specific detection of target nucleic acid in a sample. For example, modified ZFPs can be used to detect variant alleles associated with a disease or phenotype in patient samples. As an example, modified ZFPs can be used to detect the presence of particular mRNA species or cDNA in a complex mixture of mRNAs or cDNAs. As a further example, modified ZFPs can be used to quantify the copy number of a gene in a sample. For example, detection of loss of one copy of a p53 gene in a clinical sample is an indicator of susceptibility to cancer. In a further example, modified ZFPs are used to detect the presence of pathological microorganisms in clinical samples. This is achieved by using one or more modified ZFPs, as disclosed herein, that bind a target sequence in one or more genes within the microorganism to be detected. A suitable format for performing diagnostic assays employs modified ZFPs linked to a domain that allows immobilization of the ZFP on a solid support such as, for example, a microtiter plate or an ELISA plate. The immobilized ZFP is contacted with a sample suspected of containing a target nucleic acid under conditions in which binding between the modified ZFP and its target sequence can occur. Typically, nucleic acids in the sample are labeled (e.g., in the course of PCR amplification). Alternatively, unlabelled nucleic acids can be detected using a second labeled probe nucleic acid. After washing, bound, labeled nucleic acids are detected. Labeling can be direct (i.e., the probe binds directly to the target nucleic acid) or indirect (i.e., probe binds to one or more molecules which themselves bind to the target). Labels can be, for example, radioactive, fluorescent, chemiluminescent and/or enzymatic.

Modified ZFPs, as disclosed herein, can also be used in assays that link phenotype to the expression of particular genes. Current methodologies for determination of gene function rely primarily upon either over-expressing a gene of interest or removing a gene of interest from its natural biological setting, and observing the effects. The phenotypic effects resulting from over-expression or knockout are then interpreted as an indication of the role of the gene in the biological system. An exemplary animal model system for performing these types of analysis is the mouse. A transgenic mouse generally contains an introduced gene or has been genetically modified so as to up-regulate an endogenous gene. Alternatively, in a "knock-out" mouse, an endogenous gene has been deleted or its expression has been ablated. There are several problems with these existing systems, many of which are related to the fact that it is only possible to achieve "all-or-none" modulation of gene expression in these systems. The first is the limited ability to modulate expression of the gene under study (e.g., in knock-out mice, the gene under study is generally either absent from the genome or totally non-functional; while in transgenic mice which over-express a particular gene, there is generally a single level of overexpression). The second is the oft-encountered requirement for certain genes at multiple stages of development. Thus, it is not possible to determine the adult function of a particular gene, whose activity is also required during embryonic development, by generating a knock-out of that gene, since the animals containing the knock-out will not survive to adulthood.

One advantage of using ZFP-mediated regulation of a gene to determine its function, relative to the aforementioned conventional knockout analysis, is that expression of a ZFP can be placed under small molecule control. See, for example, U.S. Pat. Nos. 5,654,168; 5,789,156; 5,814,618; 5,888,981; 6,004,941; 6,087,166; 6,136,954; and co-owned WO 00/41566. By controlling expression levels of the ZFPs, one can in turn control the expression levels of a gene regulated by the ZFP to determine what degree of repression or stimulation of expression is required to achieve a given phenotypic or biochemical effect. This approach has particular value for drug development. In addition, placing ZFP expression under small molecule control allows one to surmount the aforementioned problems of embryonic lethality and developmental compensation, by switching on expression of the ZFP at a later stage in development and observing the effects in the adult animal.

Transgenic mice having target genes regulated by a modified ZFP or a ZFP fusion protein can be produced by integration of the nucleic acid encoding the modified ZFP or ZFP fusion at any site in trans to the target gene. Accordingly, homologous recombination is not required for integration of the ZFP-encoding nucleic acid. Further, because the transcriptional regulatory activity of a modified ZFP or ZFP fusion is trans-dominant, one is only required to obtain animals having one chromosomal copy of a ZFP-encoding nucleic acid. Therefore, functional knock-out animals can be produced without backcrossing.

All references cited herein are hereby incorporated by reference in their entirety for all purposes.

The following examples are presented as illustrative of, but not limiting, the claimed subject matter.

EXAMPLES

Example 1

Production of Non-Canonical Zinc Finger Binding Proteins

Synthetic genes encoding non-canonical zinc finger binding proteins are obtained following the procedure outlined in co-owned PCT WO 00/42219, with the exception that the oligonucleotide encoding the recognition helix to be modified includes a polynucleotide sequence that specifies the modified amino acid sequence. For example, for modification of finger 3 (the C-terminal-most finger of a three-finger ZFP), the sequence of oligonucleotide 6 is designed to encode the modified zinc coordination residue(s).

Example 2

Modulation of Expression of the LCK Gene with Non-Canonical ZFP

In this experiment, the designed zinc finger protein "PTP2", which recognizes the target sequence GAGGGGGCG and regulates expression of the LCK gene, was modified via substitution of the $2^{nd}$ histidine in its third finger with cysteine (to yield the protein "PTP2(H->C)". Two flanking residues were also changed to glycine to enhance the potential of the introduced cysteine to productively coordinate zinc. The sequences of the resultant zinc finger proteins were as follows:

```
PTP2:
F1
                                      (SEQ ID NO: 112)
PGKKKQHICHIQGCGKVYGRSDELTRHLRWHTGER

F2
                                      (SEQ ID NO: 113)
PFMCTWSYCGKRFTRSDHLTRHKRTHTGEK
```

-continued

F3
                                              (SEQ ID NO: 114)
     KFACPE-----CPKRFMRSDNLTRHIKTHQNKKGGS

PTP2(H → C):
F1
                                              (SEQ ID NO: 115)
PGKKKQH*I*CHIQGCGKVYGRSDELTRHLRWHTGER

F2
                                              (SEQ ID NO: 116)
     PFMCTWSYCGKRFTRSDHLTRHKRTHTGEK

F3
                                              (SEQ ID NO: 117)
     KFACPE----CPKRFMRSDNLTRHIGG*C*QNKKGGS

Bold and underlines highlight zinc-coordinating residues, and italics highlights positions changed in converting PTP2 into PTP2 (H→C).

Both ZFPs were expressed in 293 cells as fusions with a nuclear localization signal (NLS), VP16 activation domain, and a FLAG tag. The structure (e.g., order) of the fusion proteins were as follows:

| NLS | ZFP | VP16 | FLAG |

After expression of each protein in 293 cells, cellular levels of the LCK mRNA were determined relative to the level of a control RNA (18S RNA) using a PCR based "Taqman" assay. RNA levels were also determined for a control protein (NVF) lacking any ZFP (and containing only the NLS, VP16 and FLAG regions). Each experiment was performed in duplicate, and the measured RNA ratios are shown in FIG. 1. These ratios indicate that the PTP2 ZFP activates expression of the LCK gene, and that the PTP(H→C) ZFP activates LCK to even higher levels. These results illustrate the potential of substitutions at zinc-coordinating positions to provide ZFPs with enhanced cellular function. As illustrated in FIG. 1, modification of zinc-coordinating positions can enhance the cellular activity of designed zinc finger protein transcription factors.

Example 3

Modulation of Expression of a Human VEGF Gene with Modified ZFPs

This example describes the modification of two VEGF-regulating ZFPs. For each of the two ZFPs, a number of non-canonical modified ZFPs were constructed. The proteins were then tested for their ability to regulate VEGF expression and compared with the two C2H2 parental proteins.

Zinc finger proteins comprising a series of $C_2H_2$ zinc fingers, and designed to bind to the human VEGF-A gene and regulate its expression, have been described. Liu et al. (2001) *J. Biol. Chem.* 276:11,323-11,334. Two of these ZFPs (named VOP30A and VOP32B), each containing three zinc fingers, were converted to non-canonical ZFPs. VOP30A corresponds to VZ+42/+530 and VOP32B corresponds to VZ+434a in the Liu et al. reference. This was accomplished by modifying the third finger of each protein. Seven non-canonical versions of each protein were made, each comprising a different non-canonical C2HC third finger. Amino acid sequences of portions of the canonical parent ZFPs and each of the non-canonical ZFPs, beginning at histidine +7 (with respect to the start of the alpha-helix) of the third finger, are shown in Table 1.

TABLE 1

| NAME | SEQUENCE | SEQ ID NO. |
|------|----------|------------|
| C2H2 | HIKTHQNKKGGS | 11 |
| S    | HSETGCTKKGGS | 12 |
| E    | HLKSLTPCTGGS | 13 |
| K    | HKCGIQNKKGGS | 14 |
| CT   | HSENCQGKKGGS | 15 |
| C    | HIKTCQNKKGGS | 16 |
| GC   | HIKGCQNKKGGS | 17 |
| GGC  | HIGGCQNKKGGS | 18 |

Notes
1. sequences begin at +7 of the alpha helix of the third zinc finger
2. residues involved in metal coordination are bolded and underlined
3. the first row (protein designated C2H2) shows the sequence of the parental ZFPs Human embryonic kidney cells (HEK 293) were transfected with nucleic acids encoding non-canonical derivatives of the VOP30A and VOP32B fusion proteins, as well as the parent (canonical) fusion proteins. The fusion proteins also comprised a VP16 transcriptional activation domain, a nuclear localization sequence and an epitope tag.

The cells were grown in DMEM (Dulbecco's modified Eagle's medium), supplemented with 10% fetal bovine serum, in a 5% $CO_2$ incubator at 37° C. Cells were plated in 24-well plates at a density of 160,000 cells per well. A day later, when the cells were at approximately 70% confluence, plasmids encoding ZFP-VP16 fusions were introduced into the cells using LipofectAMINE 2000™ reagent (Gibco Life Technologies, Rockville, Md.) according to the manufacturer's recommendations, using 2 μl LipofectAMINE 2000™ and 1 μg plasmid DNA per well. Medium was removed and replaced with fresh medium 16 hours after transfection. Forty hours after transfection, the culture medium was harvested and assayed for VEGF-A expression. VEGF-A protein content in the culture medium was assayed using a human VEGF ELISA kit (Quanti-Glo, R&D Systems, Minneapolis, Minn.) according to the manufacturer's instructions.

Figure 2:
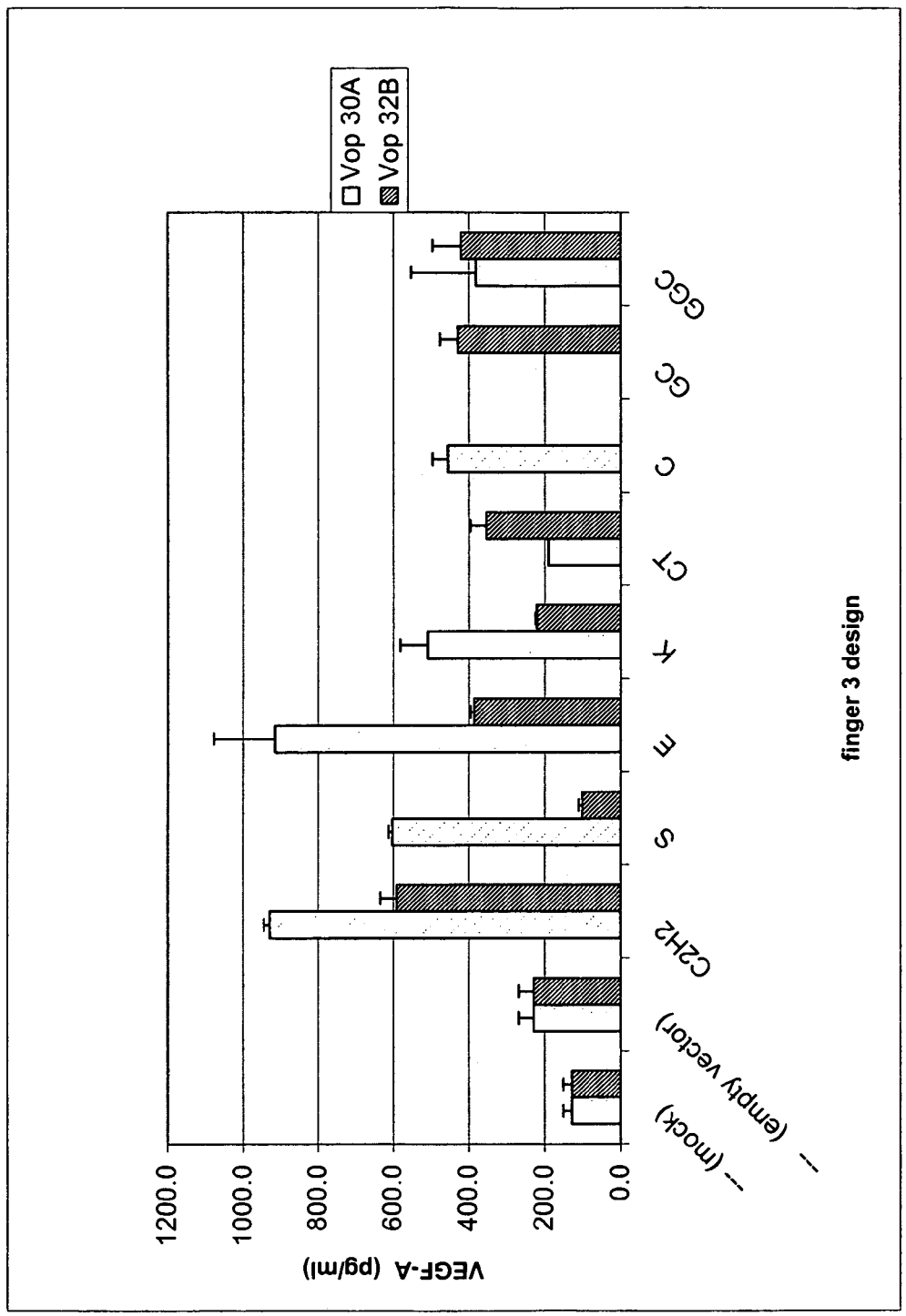
FIG. 2 shows VEGF-A levels in the culture medium of cells that had been transfected with plasmids encoding non-canonical ZFP fusion proteins comprising a VP16 activation domain, that were targeted to the VEGF gene. Mock indicates untransfected cells; empty vector indicates transfection with a DNA construct lacking sequences encoding a fusion protein; and C2H2 indicates cells transfected with plasmids encoding the canonical C2H2 VOP30A and VOP32B ZFP-VP16 fusion proteins. S, E, K, CT, C, GC and GGC indicate non-canonical derivatives of VOP30A and VOP 32B containing a C2HC zinc finger, as described in Table 1. The left-hand bar of each pair shows results for VOP30A and its non-canonical derivatives; the right-hand bar of each pair shows results for VOP32B and its non-canonical derivative. The C derivative of VOP32B and the GC derivative of VOP30A were not tested. Results are the average of two determinations.

The results, shown in FIG. 2, indicate that C2HC derivatives of both VOP 30A and VOP 32B activate VEGF expression and are thus useful as targeted exogenous regulatory molecules.

Example 4

Production of Modified Plant Zinc Finger Binding Proteins

This example describes a strategy to select amino acid sequences for plant zinc finger backbones from among existing plant zinc finger sequences, and subsequent conceptual modification of the selected plant zinc finger amino acid sequences to optimize their DNA binding ability. Oligonucleotides used in the preparation of polynucleotides encoding proteins containing these zinc fingers in tandem array are then described.

A. Selection of Plant Zinc Finger Backbones

A search was conducted for plant zinc fingers whose backbone sequences (i.e., the portion of the zinc finger outside of the −1 through +6 portion of the recognition helix) resembled that of the SP-1 consensus sequence described by Berg (1992)

Proc. Natl. Acad. Sci. USA 89:11,109-11,110. The sequences selected included the two conserved cysteine residues, a conserved basic residue (lysine or arginine) located two residues to the C-terminal side of the second (i.e. C-terminal) cysteine, a conserved phenylalanine residue located two residues to the C-terminal side of the basic residue, the two conserved histidine residues, and a conserved arginine residue located two residues to the C-terminal side of the first (i.e., N-terminal) conserved histidine. The amino acid sequences of these selected plant zinc finger backbones (compared to the SP-1 consensus sequence) are shown below, with conserved residues shown in bold and X referring to residues located at positions −1 through +6 in the recognition helix (which will differ among different proteins depending upon the target sequence):

```
SP-1 consensus:
                                            (SEQ ID NO: 19)
     YKCPECGKSFSXXXXXXXHQRTHTGEKP F1:
                                            (SEQ ID NO: 20)
KKKSKGHECPICFRVFKXXXXXXXHKRSHTGEKP F2
                                            (SEQ ID NO: 21)
     YKCTVCGKSFSXXXXXXXHKRLHTGEKP F3
                                            (SEQ ID NO: 22)
     FSCNYCQRKFYXXXXXXXHVRIH
         -5  -1     5
```

The first finger (F1) was chosen because it contained a basic sequence N-terminal to the finger that is also found adjacent to the first finger of SP-1. The finger denoted F1 is a *Petunia* sequence, the F2 and F3 fingers are *Arabidopsis* sequences.

B. Modification of Plant Zinc Finger Backbones

Two of the three plant zinc fingers (F1 and F3, above) were modified so that their amino acid sequences more closely resembled the sequence of SP-1, as follows. (Note that the sequence of SP-1 is different from the sequence denoted "SP-1 consensus.") In F3, the Y residue at position −2 was converted to a G, and the sequence QNKK (SEQ ID NO:23) was added to the C-terminus of F3. The QNKK (SEQ ID NO:23) sequence is present C-terminal to the third finger of SP-1, and permits greater flexibility of that finger, compared to fingers 1 and 2, which are flanked by the helix-capping sequence T G E K/R K/P (SEQ ID NO:24). Such flexibility can be particularly beneficial when the third finger is modified to contain a non-$C_2H_2$ backbone, as described herein. Finally, several amino acids were removed from the N-terminus of F1. The resulting zinc finger backbones had the following sequences:

```
                                            (SEQ ID NO: 25)
KSKGHECPICFRVFKXXXXXXXHKRSHTGEKP
                                            (SEQ ID NO: 26)
     YKCTVCGKSFSXXXXXXXHKRLHTGEKP
                                            (SEQ ID NO: 27)
     FSCNYCQRKFGXXXXXXXHVRIHQNKK
```

Amino acid residues denoted by X, present in the recognition portion of these zinc fingers, are designed or selected depending upon the desired target site, according to methods disclosed, for example, in co-owned WO 00/41566 and WO 00/42219, and/or references cited supra.

C. Nucleic Acid Sequences Encoding Backbones for Modified Plant ZFPs

The following polynucleotide sequences were used for design of three-finger plant ZFPs that contain the F1, F2 and F3 backbones described above. Polynucleotides encoding multi-finger ZFPs were designed according to an overlapping oligonucleotide method as described in, for example, co-owned WO 00/41566 and WO 00/42219. Oligonucleotides H1, H2 and H3 (below) comprise sequences corresponding to the reverse complement of the recognition helices of fingers 1-3 respectively; accordingly, nucleotides denoted by N vary depending upon the desired amino acid sequences of the recognition helices, which, in turn, depend upon the nucleotide sequence of the target site. Oligonucleotides PB1, PB2 and PB3 encode the beta-sheet portions of the zinc fingers, which are common to all constructs. Codons used frequently in *Arabidopsis* and *E. coli* were selected for use in these oligonucleotides.

```
H1:
                                            (SEQ ID NO: 28)
5'-CTC ACC GGT GTG AGA ACG CTT GTG NNN NNN NNN NNN
NNN NNN NNN CTT GAA AAC ACG GAA-3'

H2:
                                            (SEQ ID NO: 29)
5'-TTC ACC AGT ATG AAG ACG CTT ATG NNN NNN NNN NNN
NNN NNN NNN AGA AAA AGA CTT ACC-3'

H3:
                                            (SEQ ID NO: 30)
5'-CTT CTT GTT CTG GTG GAT ACG CAC GTG NNN NNN NNN
NNN NNN NNN NNN ACC GAA CTT ACG CTG-3'

PB1:
                                            (SEQ ID NO: 31)
5'-AAGTCTAAGGGTCACGAGTGCCCAATCTGCTTCCGTGTTTTCAAG-3'

PB2:
                                            (SEQ ID NO: 32)
5'-TCTCACACCGGTGAGAAGCCATACAAGTGCACTGTTTGTGGTAAGTC
TTTTTCT-3'

PB3:
                                            (SEQ ID NO: 33)
5'-CTTCATACTGGTGAAAAGCCATTCTCTTGCAACTACTGCCAGCGTAA
GTTCGGT-3'
```

Briefly, these six oligonucleotides are annealed and amplified by polymerase chain reaction. The initial amplification product is reamplified using primers that are complementary to the initial amplification product and that also contain 5' extensions containing restriction enzyme recognition sites, to facilitate cloning. The second amplification product is inserted into a vector containing, for example, one or more functional domains, nuclear localization sequences, and/or epitope tags. See, for example, co-owned WO 00/41566 and WO 00/42219.

Example 5

Construction of a Polynucleotide Encoding a Modified Plant Zinc Finger Protein for Binding to a Predetermined Target Sequence A modified plant zinc finger protein was designed to recognize the target sequence 5'-GAGGGGGCG-3'. Recognition helix sequences for F1, F2 and F3 were determined, as shown in Table 2, and oligonucleotides corresponding to H1, H2 and H3 above, also including sequences encoding these recognition helices, were used for PCR assembly as described above.

TABLE 2

| Finger | Target | Helix sequence | Nucleotide sequence for PCR assembly |
|---|---|---|---|
| F1 | GCG | RSDELTR SEQ ID NO: 109 | 5'CTCACCGGTGTGAGAACGCTTGTG ACGGGTCAACTCGTCAGAAGGCTTGA AAACACGGAA-3' (SEQ ID NO: 34) |
| F2 | GGG | RSDHLTR SEQ ID NO: 110 | 5'TTCACCAGTATGAAGACGCTTATG ACGGGTCAAGTGGTCAGAACGAGAAA AAGAGTTACC-3' (SEQ ID NO: 35) |
| F3 | GAG | RSDNLTR SEQ ID NO: 111 | 5'CTTCTTGTTCTGGTGGATACGCAC GTGACGGGTCAAGTTGTCAGAACGAC CGAACTTACGCTG-3' (SEQ ID NO: 36) |

Subsequent to the initial amplification, a secondary amplification was conducted, as described above, using the following primers:

PZF:
(SEQ ID NO: 37)
5'-CGG<u>GGTACC</u>AGGTAAGTCTAAGGGTCAC

PZR:
(SEQ ID NO: 38)
5'-GCGC<u>GGATCC</u>ACCCTTCTTGTTCTGGTGGATACG.

PZF includes a KpnI site (underlined) and overlaps the PB1 sequence (overlap indicated in bold). PZR includes a BamHI (underlined) site and overlaps with H3 (indicated in bold).

The secondary amplification product is digested with Kpn I and Bam HI and inserted into an appropriate vector (e.g., YCF3, whose construction is described below) to construct an expression vector encoding a modified plant ZFP fused to a functional domain, for modulation of gene expression in plant cells.

Example 6

Construction of Vectors for Expression of Modified Plant ZFPs

Figure 3A:
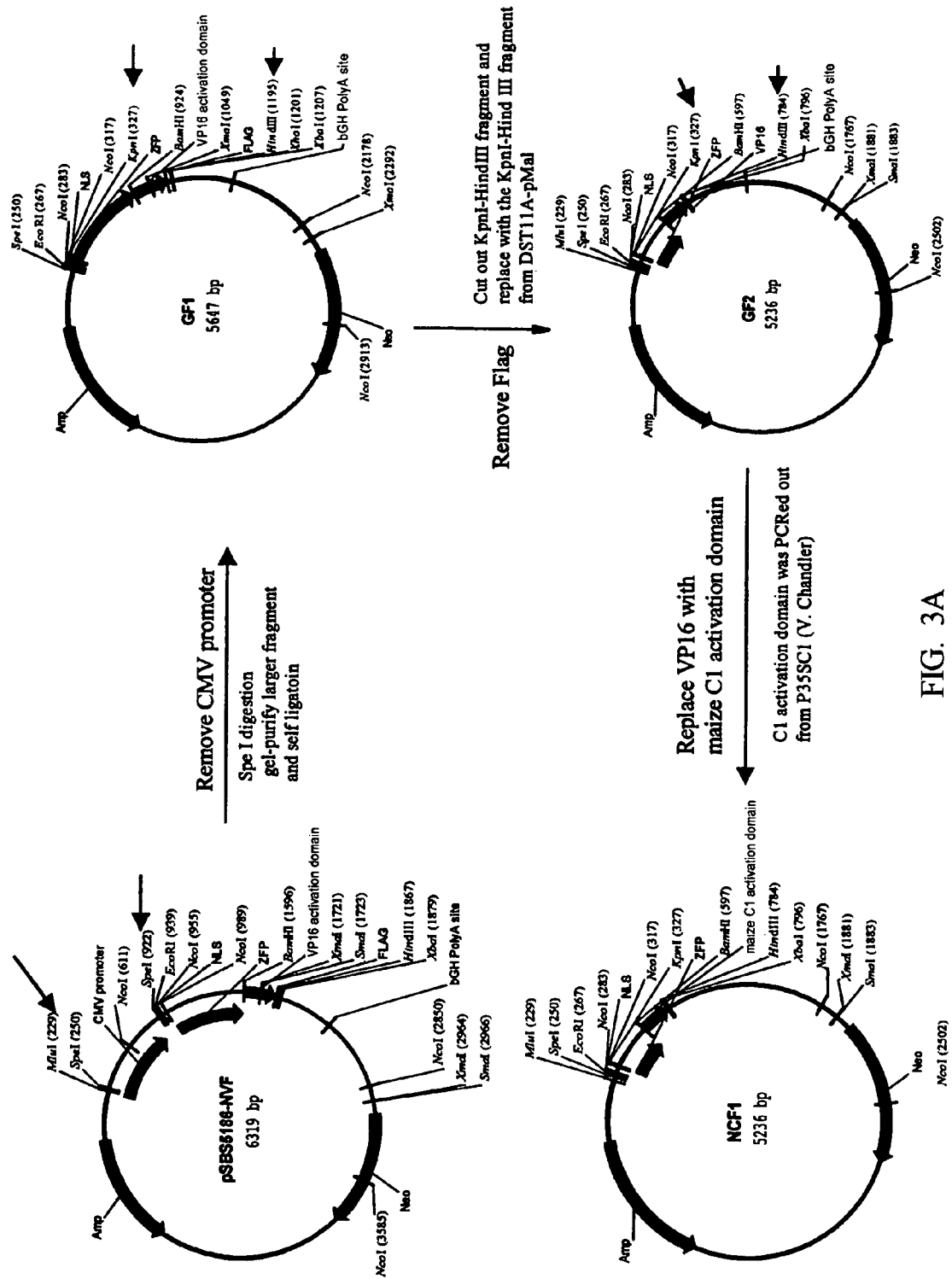
FIG. 3, panels A and B, are schematics depicting construction of the YCF3 expression vector useful in expressing modified ZFPs.
Figure 3B:
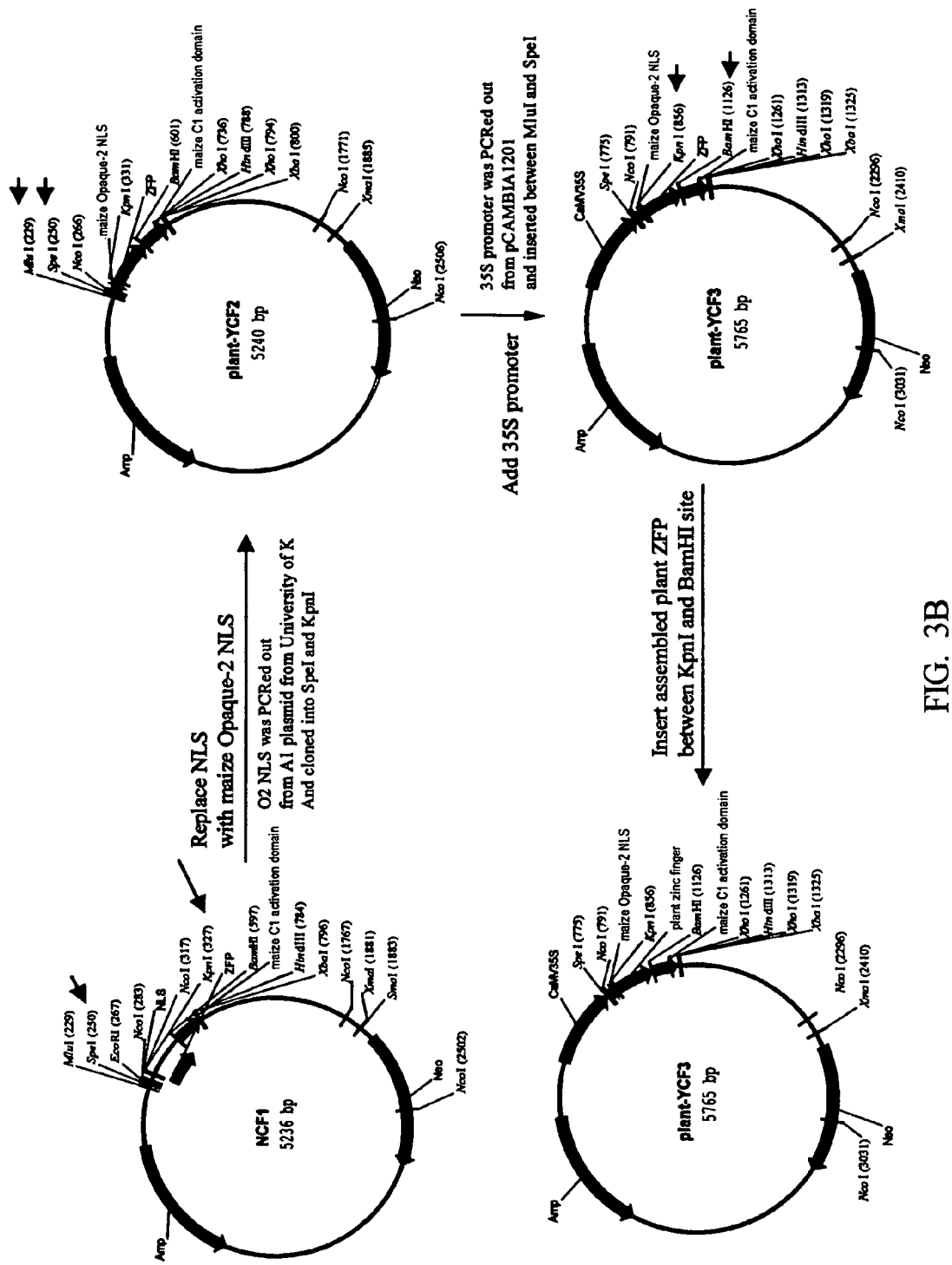

YCF3 was generated as shown in FIG. 3. The starting construct was a plasmid containing a CMV promoter, a SV40 nuclear localization sequence (NLS), a ZFP DNA binding domain, a Herpesvirus VP16 transcriptional activation domain and a FLAG epitope tag (pSB5186-NVF). This construct was digested with SpeI to remove the CMV promoter. The larger fragment was gel-purified and self-ligated to make a plasmid termed GF1. GF1 was then digested with KpnI and HindIII, releasing sequences encoding the ZFP domain, the VP16 activation domain, and the FLAG epitope tag, then the larger fragment was ligated to a KpnI/HindIII fragment containing sequences encoding a ZFP binding domain and a VP16 activation domain, named GF2. This resulted in deletion of sequences encoding the FLAG tag from the construct.

GF2 was digested with BarnHI and HindIII, releasing a small fragment encoding the VP16 activation domain, and the larger fragment was purified and ligated to a BamHI/HindIII digested PCR fragment containing the maize C1 activation domain (Goff et al. (1990) *EMBO J.* 9:2517-2522) (KpnI and HindIII sites were introduced into the PCR fragment through KpnI and HindIII site-containing primers) to generate NCF1. A PCR fragment containing a Maize Opaque-2 NLS was digested with SpeI/KpnI and ligated to the larger fragment from KpnI/SpeI digested NCF1 to produce YCF2. YCF2 was then digested with MluI and SpeI and the larger fragment was ligated to an MluI and SpeI digested PCR fragment containing the plant-derived CaMV 35S promoter (MluI and SpeI sites were introduced into the PCR fragment through MluI or SpeI site containing primers) to generate the YCF3 vector.

Sequences encoding modified plant ZFP binding domains can be inserted, as KpnI/BamHI fragments, into KpnI/BamHI-digested YCF3 to generate constructs encoding ZFP-functional domain fusion proteins for modulation of gene expression in plant cells. For example, a series of modified plant ZFP domains, described in Example 5 infra, were inserted into KpnI/BamHI-digested YCF3 to generate expression vectors encoding modified plant ZFP-activation domain fusion polypeptides that enhance expression of the *Arabidopsis thaliana* GMT gene.

Example 7

Modified ZFP Designs for Regulation of an *Arabidopsis thaliana* Gamma Tocopherol Methyltransferase (GMT) Gene Modified zinc finger proteins were designed to recognize various target sequences in the *Arabidopsis* GMT gene (GenBank Accession Number AAD38271). These proteins were modified in two ways. First, they contained a plant backbone as described in Example 4. Second, they contained a non-canonical ($C_2HC$) third zinc finger in which the second zinc coordinating histidine of a canonical $C_2H_2$ structure was converted to a cysteine. Table 3 shows the nucleotide sequences of the various GMT target sites, and the amino acid sequences of zinc fingers that recognize the target sites. Sequences encoding these binding domains were prepared as described in Example 4 and inserted into YCF3 as described in Example 6.

TABLE 3

| ZFP # | Target | F1 | F2 | F3 |
|---|---|---|---|---|
| 1 | GTGGACGAGT (SEQ ID NO: 39) | RSDNLAR (SEQ ID NO: 40) | DRSNLTR (SEQ ID NO: 41) | RSDALTR (SEQ ID NO: 42) |
| 2 | CGGGATGGGT (SEQ ID NO: 43) | RSDHLAR (SEQ ID NO: 44) | TSGNLVR (SEQ ID NO: 45) | RSDHLRE (SEQ ID NO: 46) |
| 3 | TGGTGGGTGT (SEQ ID NO: 47) | RSDALTR (SEQ ID NO: 48) | RSDHLTT (SEQ ID NO: 49) | RSDHLTT (SEQ ID NO: 50) |
| 4 | GAAGAGGATT (SEQ ID NO: 51) | QSSNLAR (SEQ ID NO: 52) | RSDNLAR (SEQ ID NO: 53) | QSGNLTR (SEQ ID NO: 54) |

TABLE 3-continued

| ZFP # | Target | F1 | F2 | F3 |
|---|---|---|---|---|
| 5 | GAGGAAGGGG (SEQ ID NO: 55) | RSDHLAR (SEQ ID NO: 56) | QSGNLAR (SEQ ID NO: 57) | RSDNLTR (SEQ ID NO: 58) |
| 6 | TGGGTAGTC (SEQ ID NO: 59) | ERGTLAR (SEQ ID NO: 60) | QSGSLTR (SEQ ID NO: 61) | RSDHLTT (SEQ ID NO: 62) |
| 7 | GGGGAAAGGG (SEQ ID NO: 63) | RSDHLTQ (SEQ ID NO: 64) | QSGNLAR (SEQ ID NO: 65) | RSDHLSR (SEQ ID NO: 66) |
| 8 | GAAGAGGGTG (SEQ ID NO: 67) | QSSHLAR (SEQ ID NO: 68) | RSDNLAR (SEQ ID NO: 69) | QSGNLAR (SEQ ID NO: 70) |
| 9 | GAGGAGGATG (SEQ ID NO: 71) | QSSNLQR (SEQ ID NO: 72) | RSDNALR (SEQ ID NO: 73) | RSDNLQR (SEQ ID NO: 74) |
| 10 | GAGGAGGAGG (SEQ ID NO: 75) | RSDNALR (SEQ ID NO: 76) | RSDNLAR (SEQ ID NO: 77) | RSDNLTR (SEQ ID NO: 78) |
| 11 | GTGGCGGCTG (SEQ ID NO: 79) | QSSDLRR (SEQ ID NO: 80) | RSDELQR (SEQ ID NO: 81) | RSDALTR (SEQ ID NO: 82) |
| 12 | TGGGGAGAT (SEQ ID NO: 83) | QSSNLAR (SEQ ID NO: 84) | QSGHLQR (SEQ ID NO: 85) | RSDHLTT (SEQ ID NO: 86) |
| 13 | GAGGAAGCT (SEQ ID NO: 87) | QSSDLRR (SEQ ID NO: 88) | QSGNLAR (SEQ ID NO: 89) | RSDNLTR (SEQ ID NO: 90) |
| 14 | GCTTGTGGCT (SEQ ID NO: 91) | DRSHLTR (SEQ ID NO: 92) | TSGHLTT (SEQ ID NO: 93) | QSSDLTR (SEQ ID NO: 94) |
| 15 | GTAGTGGATG (SEQ ID NO: 95) | QSSNLAR (SEQ ID NO: 96) | RSDALSR (SEQ ID NO: 97) | QSGSLTR (SEQ ID NO: 98) |
| 16 | GTGTGGGATT (SEQ ID NO: 99) | QSSNLAR (SEQ ID NO: 100) | RSDHLTT (SEQ ID NO: 101) | RSDALTR (SEQ ID NO: 102) |

Example 8

Modulation of Expression of an *Arabidopsis thaliana* Gamma Tocopherol Methyltransferase (GMT) Gene

*Arabidopsis thaliana* protoplasts were prepared and transfected with plasmids encoding modified ZFP-activation domain fusion polypeptides. Preparation of protoplasts and polyethylene glycol-mediated transfection were performed as described. Abel et al. (1994) *Plant Journal* 5:421-427. The different plasmids contained the modified plant ZFP binding domains described in Table 3, inserted as KpnI/BamHI fragments into YCF3.

Figure 4:
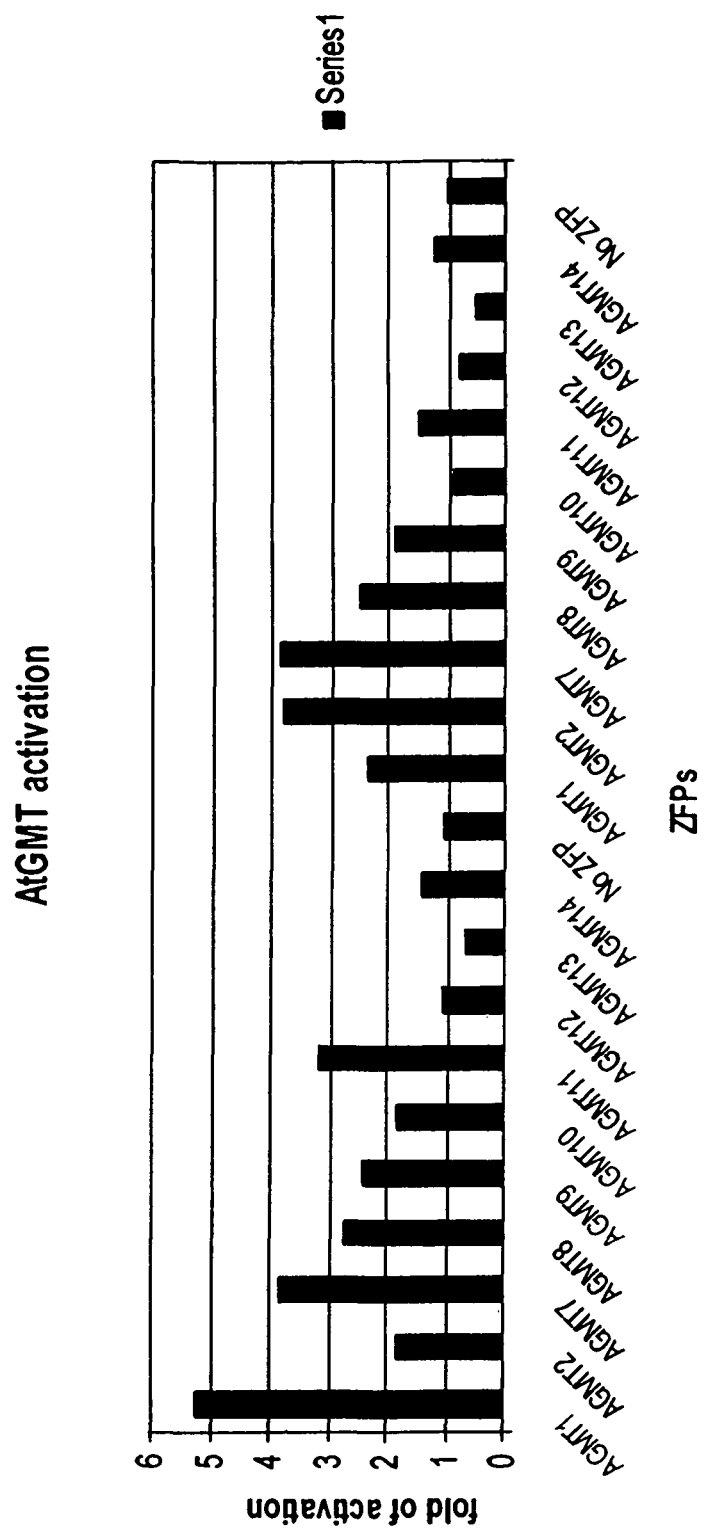
FIG. 4 shows the results of analysis of GMT mRNA in RNA isolated from *Arabidopsis thaliana* protoplasts that had been transfected with constructs encoding fusion of a transcriptional activation domain with various modified plant ZFPs. Results are expressed as GMT mRNA normalized to 18S rRNA. AGMT numbers on the abscissa refer to the modified plant ZFP binding domains shown in Table 2. Duplicate TaqMan® analyses are shown for each RNA sample.

At 18 hours after transfection, RNA was isolated from transfected protoplasts, using an RNA extraction kit from Qiagen (Valencia, Calif.) according to the manufacturer's instructions. The RNA was then treated with DNase (RNase-free), and analyzed for GMT mRNA content by real-time PCR (TaqMan®). Table 4 shows the sequences of the primers and probe used for TaqMan® analysis. Results for GMT mRNA levels were normalized to levels of 18S rRNA. These normalized results are shown in FIG. 4 as fold-activation of GMT mRNA levels, compared to protoplasts transfected with carrier DNA (denoted "No ZFP" in FIG. 4). The results indicate that expression of the GMT gene was enhanced in protoplasts that were transfected with plasmids encoding fusions between a transcriptional activation domain and a modified plant ZFP binding domain targeted to the GMT gene.

TABLE 4

| | SEQUENCE | |
|---|---|---|
| GMT forward primer | 5'-AATGATCTCGCGGCTGCT-3' | (SEQ ID NO: 103) |
| GMT reverse primer | 5'-GAATGGCTGATCCAACGCAT-3' | (SEQ ID NO: 104) |
| GMT probe | 5'-TCACTCGCTCATAAGGCTTCCTTGCAAGT-3' | (SEQ ID NO: 105) |
| 18S forward primer | 5'-TGCAACAAACCCCGACTTATG-3' | (SEQ ID NO: 106) |
| 18S reverse primer | 5'-CCCGCGTCGACCTTTTATC-3' | (SEQ ID NO: 107) |
| 18S probe | 5'-AATAAATGCGTCCCTT-3' | (SEQ ID NO: 108) |

Although the foregoing methods and compositions have been described in detail for purposes of clarity of understanding, certain modifications, as known to those of skill in the art, can be practiced within the scope of the appended claims. All publications and patent documents cited herein are hereby incorporated by reference in their entirety for all purposes to the same extent as if each were so individually denoted.

What is claimed is:

1. A method of modulating expression of a gene in a plant cell or in an isolated mammalian cell, the method comprising the step of expressing, in the cell, a non-naturally-occurring zinc-finger binding protein comprising a non-canonical zinc finger comprising the sequence $X_3$-Cys-$X_{2-4}$-Cys-$X_{12}$-His-$X_{1-7}$-Z-$X_4$(SEQ ID NO:121), where X is any amino acid and Z is C, where residues 6 to 12 of $X_{12}$ are engineered to bind to a target nucleic acid sequence, and wherein $X_{1-7}$ is selected from the group consisting of SETG (residues 2-5 of SEQ ID NO:12), LKSLTP (residues 2-7 of SEQ ID NO:13), SEN, VRI, KRS, KRL, LRW, ITT, IKG and IGG.

2. The method of claim 1, wherein the non-naturally-occurring zinc-finger binding protein further comprises a functional domain.

3. The method of claim 2, wherein the functional domain is an endonuclease.

4. The non-naturally occurring zinc finger binding proteins of claim 2, wherein the functional domain is a repressive domain.

5. The non-naturally occurring zinc finger binding proteins of claim 2, wherein the functional domain is an activation domain.

6. The method of claim 1, wherein the gene is in a plant cell.

* * * * *

```
                              SEQUENCE LISTING

<160> NUMBER OF SEQ ID NOS: 147

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid and this region may encompass
      2-4 residues
<220> FEATURE:
<221> NAME/KEY: MOD_RES
<222> LOCATION: (7)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid and this region may encompass
      3-5 residues

<400> SEQUENCE: 1

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      canonical consensus sequence
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 2

Xaa Xaa Xaa Cys Xaa Xaa Xaa Xaa Cys Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa
```

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      target sequence

<400> SEQUENCE: 3 ggcgtagac                                                          9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      target segment oligonucleotide

<400> SEQUENCE: 4 ggcgacgta                                                          9

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 5

Thr Gly Glu Lys Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 6

Gly Gly Gly Gly Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 7

Gly Gly Arg Arg Gly Gly Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 8

Leu Arg Gln Arg Asp Gly Glu Arg Pro
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 9

Leu Arg Gln Lys Asp Gly Gly Gly Ser Glu Arg Pro
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide linker peptide

<400> SEQUENCE: 10

Leu Arg Gln Lys Asp Gly Gly Gly Ser Gly Gly Gly Ser Glu Arg Pro
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion C2H2 peptide

<400> SEQUENCE: 11

His Ile Lys Thr His Gln Asn Lys Lys Gly Gly Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion S peptide

<400> SEQUENCE: 12

His Ser Glu Thr Gly Cys Thr Lys Lys Gly Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion E peptide

<400> SEQUENCE: 13

His Leu Lys Ser Leu Thr Pro Cys Thr Gly Gly Ser
1               5                   10

<210> SEQ ID NO 14
<211> LENGTH: 12
<212> TYPE: PRT
<213> ORGANISM: Artificial Sequence

```
<220> FEATURE:
<223> OTHER INFORMATION: Description of Artificial Sequence: Synthetic
      ZFP portion K peptide

<400> SEQUENCE: 14

His Lys Cys Gly Ile Gln Asn Lys Lys Gly Gly Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion CT peptide

<400> SEQUENCE: 15

His Ser Glu Asn Cys Gln Gly Lys Lys Gly Gly Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion C peptide

<400> SEQUENCE: 16

His Ile Lys Thr Cys Gln Asn Lys Lys Gly Gly Ser
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion GC peptide

<400> SEQUENCE: 17

His Ile Lys Gly Cys Gln Asn Lys Lys Gly Gly Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      ZFP portion GGC peptide

<400> SEQUENCE: 18

His Ile Gly Gly Cys Gln Asn Lys Lys Gly Gly Ser
1               5                   10

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      SP-1 consensus sequence
<220> FEATURE:
<221> NAME/KEY: MOD_RES
<222> LOCATION: (12)..(18)
<223> OTHER INFORMATION: Any amino acid

<400> SEQUENCE: 19
```

```
Tyr Lys Cys Pro Glu Cys Gly Lys Ser Phe Ser Xaa Xaa Xaa Xaa
1               5                   10                  15

Xaa Xaa His Gln Arg Thr His Thr Gly Glu Lys Pro
            20                  25
```

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic
      backbone F1 polypeptide
<220> FEATURE:
<221> NAME/KEY: MOD_RES
<222> LOCATION: (18)..(24)
<223> OTHER INFORMATION: Any amino acid

<400> SEQUENCE: 20

```
Lys Lys Lys Ser Lys Gly His Glu Cys Pro Ile Cys Phe Arg Val Phe
1               5                   10                  15

Lys Xaa Xaa Xaa Xaa Xaa Xaa Xaa His Lys Arg Ser His Thr Gly Glu
            20                  25                  30

Lys Pro
```

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      backbone F2 peptide
<220> FEATURE:
<221> NAME/KEY: MOD_RES
<222> LOCATION: (12)..(18)
<223> OTHER INFORMATION: Any amino acid

<400> SEQUENCE: 21

```
Tyr Lys Cys Thr Val Cys Gly Lys Ser Phe Ser Xaa Xaa Xaa Xaa Xaa
1               5                   10                  15

Xaa Xaa His Lys Arg Leu His Thr Gly Glu Lys Pro
            20                  25
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      backbone F3 peptide
<220> FEATURE:
<221> NAME/KEY: MOD_RES
<222> LOCATION: (12)..(18)
<223> OTHER INFORMATION: Any amino acid

<400> SEQUENCE: 22

```
Phe Ser Cys Asn Tyr Cys Gln Arg Lys Phe Tyr Xaa Xaa Xaa Xaa Xaa
1               5                   10                  15

Xaa Xaa His Val Arg Ile His
            20
```

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic peptide sequence added to C-terminus of F3

<400> SEQUENCE: 23

Gln Asn Lys Lys
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      helix-capping peptide
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (5)..(5)
<223> OTHER INFORMATION: Lys or Pro

<400> SEQUENCE: 24

Thr Gly Glu Xaa Xaa
1               5

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      zinc finger backbone polypeptide
<220> FEATURE:
<221> NAME/KEY: MOD_RES
<222> LOCATION: (16)..(22)
<223> OTHER INFORMATION: Any amino acid

<400> SEQUENCE: 25

Lys Ser Lys Gly His Glu Cys Pro Ile Cys Phe Arg Val Phe Lys Xaa
1               5                   10                  15

Xaa Xaa Xaa Xaa Xaa Xaa His Lys Arg Ser His Thr Gly Glu Lys Pro
            20                  25                  30

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      zinc finger backbone peptide
<220> FEATURE:
<221> NAME/KEY: MOD_RES
<222> LOCATION: (12)..(18)
<223> OTHER INFORMATION: Any amino acid

<400> SEQUENCE: 26

Tyr Lys Cys Thr Val Cys Gly Lys Ser Phe Ser Xaa Xaa Xaa Xaa Xaa
1               5                   10                  15

Xaa Xaa His Lys Arg Leu His Thr Gly Glu Lys Pro
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      zinc finger backbone peptide

```
<220> FEATURE:
<221> NAME/KEY: MOD_RES
<222> LOCATION: (12)..(18)
<223> OTHER INFORMATION: Any amino acid

<400> SEQUENCE: 27

Phe Ser Cys Asn Tyr Cys Gln Arg Lys Phe Gly Xaa Xaa Xaa Xaa Xaa
1               5                   10                  15

Xaa Xaa His Val Arg Ile His Gln Asn Lys Lys
            20                  25

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide H1
<220> FEATURE:
<221> NAME/KEY: modified_base
<222> LOCATION: (25)..(45)
<223> OTHER INFORMATION: a, c, g or t

<400> SEQUENCE: 28
ctcaccggtg tgagaacgct tgtgnnnnnn nnnnnnnnnn nnnncttga aaacacggaa        60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide H2
<220> FEATURE:
<221> NAME/KEY: modified_base
<222> LOCATION: (25)..(45)
<223> OTHER INFORMATION: a, c, g or t

<400> SEQUENCE: 29
ttcaccagta tgaagacgct tatgnnnnnn nnnnnnnnnn nnnnagaaa aagacttacc         60

<210> SEQ ID NO 30
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide H23
<220> FEATURE:
<221> NAME/KEY: modified_base
<222> LOCATION: (28)..(48)
<223> OTHER INFORMATION: a, c, g or t

<400> SEQUENCE: 30
cttcttgttc tggtggatac gcacgtgnnn nnnnnnnnn nnnnnnnac cgaacttacg         60 ctg                                                                     63

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide PB1

<400> SEQUENCE: 31
aagtctaagg gtcacgagtg cccaatctgc ttccgtgttt tcaag                       45
```

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide PB2

<400> SEQUENCE: 32
tctcacaccg gtgagaagcc atacaagtgc actgtttgtg gtaagtcttt ttct            54

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide PB3

<400> SEQUENCE: 33
cttcatactg gtgaaaagcc attctcttgc aactactgcc agcgtaagtt cggt            54

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      PCR assembly finger F1 oligonucleotide

<400> SEQUENCE: 34
ctcaccggtg tgagaacgct tgtgacgggt caactcgtca gaacgcttga aaacacggaa      60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      PCR assembly finger F2 oligonucleotide

<400> SEQUENCE: 35
ttcaccagta tgaagacgct tatgacgggt caagtggtca gaacgagaaa aagacttacc      60

<210> SEQ ID NO 36
<211> LENGTH: 63
<212> TYPE: DNA
<213> ORGANISM: Artificial Sequence
<220> FEATURE:
<223> OTHER INFORMATION: Description of Artificial Sequence: Synthetic
      PCR assembly finger F3 oligonucleotide

<400> SEQUENCE: 36
cttcttgttc tggtggatac gcacgtgacg ggtcaagttg tcagaacgac cgaacttacg      60
ctg                                                                   63

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PZF

<400> SEQUENCE: 37
cggggtacca ggtaagtcta agggtcac                                        28

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer PZR

<400> SEQUENCE: 38
gcgcggatcc acccttcttg ttctggtgga tacg                               34

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #1 target oligonucleotide

<400> SEQUENCE: 39
gtggacgagt                                                          10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #1 F1 peptide

<400> SEQUENCE: 40

Arg Ser Asp Asn Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #1 F2 peptide

<400> SEQUENCE: 41

Asp Arg Ser Asn Leu Thr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #1 F3 peptide

<400> SEQUENCE: 42

Arg Ser Asp Ala Leu Thr Arg
1               5

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #2 target oligonucleotide

<400> SEQUENCE: 43
cgggatgggt                                                          10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #2 F1 peptide

<400> SEQUENCE: 44

Arg Ser Asp His Leu Ala Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #2 F2 peptide

<400> SEQUENCE: 45

Thr Ser Gly Asn Leu Val Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #2 F3 peptide

<400> SEQUENCE: 46

Arg Ser Asp His Leu Arg Glu
1               5

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #3 target oligonucleotide

<400> SEQUENCE: 47
tggtgggtgt                                                          10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #3 F1 peptide

<400> SEQUENCE: 48

Arg Ser Asp Ala Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic

```
                        ZFP #3 F2 peptide

<400> SEQUENCE: 49

Arg Ser Asp His Leu Thr Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #3 F3 peptide

<400> SEQUENCE: 50

Arg Ser Asp His Leu Thr Thr
1               5

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #4 target oligonucleotide

<400> SEQUENCE: 51
gaagaggatt                                                              10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #4 F1 peptide

<400> SEQUENCE: 52

Gln Ser Ser Asn Leu Ala Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #4 F2 peptide

<400> SEQUENCE: 53

Arg Ser Asp Asn Leu Ala Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #4 F3 peptide

<400> SEQUENCE: 54

Gln Ser Gly Asn Leu Thr Arg
1               5

<210> SEQ ID NO 55
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      ZFP #5 target oligonucleotide

<400> SEQUENCE: 55
gaggaagggg                                                               10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #5 F1 peptide

<400> SEQUENCE: 56

Arg Ser Asp His Leu Ala Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #5 F2 peptide

<400> SEQUENCE: 57

Gln Ser Gly Asn Leu Ala Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #5 F3 peptide

<400> SEQUENCE: 58

Arg Ser Asp Asn Leu Thr Arg
1               5

<210> SEQ ID NO 59
<211> LENGTH: 9
<212> TYPE: DNA
<213> ORGANISM: Artificial Sequence
<220> FEATURE:
<223> OTHER INFORMATION: Description of Artificial Sequence: Synthetic
      ZFP #6 target oligonucleotide

<400> SEQUENCE: 59 tgggtagtc                                                                9

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #6 F1 peptide

<400> SEQUENCE: 60

Glu Arg Gly Thr Leu Ala Arg
1               5
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #6 F2 peptide

<400> SEQUENCE: 61

Gln Ser Gly Ser Leu Thr Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #6 F3 peptide

<400> SEQUENCE: 62

Arg Ser Asp His Leu Thr Thr
1               5

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #7 target oligonucleotide

<400> SEQUENCE: 63
ggggaaaggg                                                          10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #7 F1 peptide

<400> SEQUENCE: 64

Arg Ser Asp His Leu Thr Gln
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #7 F2 peptide

<400> SEQUENCE: 65

Gln Ser Gly Asn Leu Ala Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #7 F3 peptide

<400> SEQUENCE: 66

Arg Ser Asp His Leu Ser Arg
1               5

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #8 target oligonucleotide

<400> SEQUENCE: 67
gaagagggtg                                                          10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #8 F1 peptide

<400> SEQUENCE: 68

Gln Ser Ser His Leu Ala Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #8 F2 peptide

<400> SEQUENCE: 69

Arg Ser Asp Asn Leu Ala Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #8 F3 peptide

<400> SEQUENCE: 70

Gln Ser Gly Asn Leu Ala Arg
1               5

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #9 target oligonucleotide

<400> SEQUENCE: 71
gaggaggatg                                                          10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic

```
                         ZFP #9 F1 peptide

<400> SEQUENCE: 72

Gln Ser Ser Asn Leu Gln Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #9 F2 peptide

<400> SEQUENCE: 73

Arg Ser Asp Asn Ala Leu Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #9 F3 peptide

<400> SEQUENCE: 74

Arg Ser Asp Asn Leu Gln Arg
1               5

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #10 target oligonucleotide

<400> SEQUENCE: 75
gaggaggagg                                                          10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #10 F1 peptide

<400> SEQUENCE: 76

Arg Ser Asp Asn Ala Leu Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #10 F2 peptide

<400> SEQUENCE: 77

Arg Ser Asp Asn Leu Ala Arg
1               5

<210> SEQ ID NO 78
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      ZFP #10 F3 peptide

<400> SEQUENCE: 78

Arg Ser Asp Asn Leu Thr Arg
1               5

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #11 target oligonucleotide

<400> SEQUENCE: 79
gtggcggctg                                                          10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #11 F1 peptide

<400> SEQUENCE: 80

Gln Ser Ser Asp Leu Arg Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #11 F2 peptide

<400> SEQUENCE: 81

Arg Ser Asp Glu Leu Gln Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #11 F3 peptide

<400> SEQUENCE: 82

Arg Ser Asp Ala Leu Thr Arg
1               5

<210> SEQ ID NO 83
<211> LENGTH: 9
<212> TYPE: DNA
<213> ORGANISM: Artificial Sequence
<220> FEATURE:
<223> OTHER INFORMATION: Description of Artificial Sequence: Synthetic
      ZFP #12 target oligonucleotide

<400> SEQUENCE: 83 tggggagat                                                            9
```

```
<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #12 F1 peptide

<400> SEQUENCE: 84

Gln Ser Ser Asn Leu Ala Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #12 F2 peptide

<400> SEQUENCE: 85

Gln Ser Gly His Leu Gln Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #12 F3 peptide

<400> SEQUENCE: 86

Arg Ser Asp His Leu Thr Thr
1               5

<210> SEQ ID NO 87
<211> LENGTH: 9
<212> TYPE: DNA
<213> ORGANISM: Artificial Sequence
<220> FEATURE:
<223> OTHER INFORMATION: Description of Artificial Sequence: Synthetic
      ZFP #13 target oligonucleotide

<400> SEQUENCE: 87 gaggaagct                                                                9

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #13 F1 peptide

<400> SEQUENCE: 88

Gln Ser Ser Asp Leu Arg Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #13 F2 peptide

<400> SEQUENCE: 89
```

```
Gln Ser Gly Asn Leu Ala Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #13 F3 peptide

<400> SEQUENCE: 90

Arg Ser Asp Asn Leu Thr Arg
1               5

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #14 target oligonucleotide

<400> SEQUENCE: 91
gcttgtggct                                                          10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #14 F1 peptide

<400> SEQUENCE: 92

Asp Arg Ser His Leu Thr Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #14 F2 peptide

<400> SEQUENCE: 93

Thr Ser Gly His Leu Thr Thr
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #14 F3 peptide

<400> SEQUENCE: 94

Gln Ser Ser Asp Leu Thr Arg
1               5

<210> SEQ ID NO 95
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      ZFP #15 target oligonucleotide

<400> SEQUENCE: 95
gtagtggatg                                                          10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #15 F1 peptide

<400> SEQUENCE: 96

Gln Ser Ser Asn Leu Ala Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #15 F2 peptide

<400> SEQUENCE: 97

Arg Ser Asp Ala Leu Ser Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #15 F3 peptide

<400> SEQUENCE: 98

Gln Ser Gly Ser Leu Thr Arg
1               5

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFP #16 target oligonucleotide

<400> SEQUENCE: 99
gtgtgggatt                                                          10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #16 F1 peptide

<400> SEQUENCE: 100

Gln Ser Ser Asn Leu Ala Arg
1               5

<210> SEQ ID NO 101
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      ZFP #16 F2 peptide

<400> SEQUENCE: 101

Arg Ser Asp His Leu Thr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      ZFP #16 F3 peptide

<400> SEQUENCE: 102

Arg Ser Asp Ala Leu Thr Arg
1               5

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      GMT forward primer

<400> SEQUENCE: 103
aatgatctcg cggctgct                                                 18

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      GMT reverse primer

<400> SEQUENCE: 104
gaatggctga tccaacgcat                                               20

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      GMT probe

<400> SEQUENCE: 105
tcactcgctc ataaggcttc cttccaagt                                     29

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      18S forward primer

<400> SEQUENCE: 106
tgcaacaaac cccgacttat g                                             21

<210> SEQ ID NO 107
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      18S reverse primer

<400> SEQUENCE: 107
cccgcgtcga ccttttatc                                                19

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      18S probe

<400> SEQUENCE: 108
aataaatgcg tccctt                                                   16

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      F1 helix sequence

<400> SEQUENCE: 109

Arg Ser Asp Glu Leu Thr Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      F2 helix sequence

<400> SEQUENCE: 110

Arg Ser Asp His Leu Thr Arg
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      F3 helix sequence

<400> SEQUENCE: 111

Arg Ser Asp Asn Leu Thr Arg
1               5

<210> SEQ ID NO 112
<211> LENGTH: 35
<212> TYPE: PRT
<213> ORGANISM: Artificial Sequence
<220> FEATURE:
<223> OTHER INFORMATION: Description of Artificial Sequence: Synthetic
      poly PTP2 F1 peptide

<400> SEQUENCE: 112

Pro Gly Lys Lys Lys Gln His Ile Cys His Ile Gln Gly Cys Gly Lys
1               5                   10                  15
```

Val Tyr Gly Arg Ser Asp Glu Leu Thr Arg His Leu Arg Trp His Thr
            20                  25                  30

Gly Glu Arg
        35

<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence: Synthetic
      PTP2 F2 polypeptide

<400> SEQUENCE: 113

Pro Phe Met Cys Thr Trp Ser Tyr Cys Gly Lys Arg Phe Thr Arg Ser
1               5                   10                  15

Asp His Leu Thr Arg His Lys Arg Thr His Thr Gly Glu Lys
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: Description of Artificial Sequence: Synthetic
      PTP2 F3 polypeptide

<400> SEQUENCE: 114

Lys Phe Ala Cys Pro Glu Cys Pro Lys Arg Phe Met Arg Ser Asp Asn
1               5                   10                  15

Leu Thr Arg His Ile Lys Thr His Gln Asn Lys Lys Gly Gly Ser
            20                  25                  30

<210> SEQ ID NO 115
<211> LENGTH: 35
<212> TYPE: PRT
<213> ORGANISM: Artificial Sequence
<220> FEATURE:
<223> OTHER INFORMATION: Description of Artificial Sequence: Synthetic
      PTP2(H->C) F1 polypeptide

<400> SEQUENCE: 115

Pro Gly Lys Lys Lys Gln His Ile Cys His Ile Gln Gly Cys Gly Lys
1               5                   10                  15

Val Tyr Gly Arg Ser Asp Glu Leu Thr Arg His Leu Arg Trp His Thr
            20                  25                  30

Gly Glu Arg
        35

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      PTP2(H->C) F2 polypeptide

<400> SEQUENCE: 116

Pro Phe Met Cys Thr Trp Ser Tyr Cys Gly Lys Arg Phe Thr Arg Ser
1               5                   10                  15

Asp His Leu Thr Arg His Lys Arg Thr His Thr Gly Glu Lys
            20                  25                  30

```
<210> SEQ ID NO 117
<211> LENGTH: 31
<212> TYPE: PRT
<213> ORGANISM: Artificial Sequence
<220> FEATURE:
<223> OTHER INFORMATION: Description of Artificial Sequence: Synthetic
      PTP2(H->C) F3 polypeptide

<400> SEQUENCE: 117

Lys Phe Ala Cys Pro Glu Cys Pro Lys Arg Phe Met Arg Ser Asp Asn
1               5                   10                  15

Leu Thr Arg His Ile Gly Gly Cys Gln Asn Lys Lys Gly Gly Ser
                20                  25                  30

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 118

Xaa Xaa Xaa Xaa Xaa Xaa Xaa Xaa Cys Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
                20                  25                  30

Xaa Xaa

<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
```

```
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 119

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
                20                  25                  30

Xaa Xaa

<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 120

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
                20                  25                  30

Xaa Xaa

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
```

```
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 121

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa
            20                  25                  30

Xaa Xaa

<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 122
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa His Xaa Xaa
                20                  25                  30

Xaa Xaa
```

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 123

```
Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Xaa His Xaa Xaa
                20                  25                  30

Xaa Xaa
```

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:

<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
    1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 124

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa
            20                  25                  30

Xaa Xaa

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
    non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
    2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
    1-7 residues
<220> FEATURE:
<221> NAME/KEY: MOD_RES
<222> LOCATION: (31)..(34)
<223> OTHER INFORMATION: Any amino acid

<400> SEQUENCE: 125

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 126
<211> LENGTH: 34

```
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 126

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa
            20                  25                  30

Xaa Xaa

<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
```

<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 127

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 128

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES

```
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
     2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
     1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 129

Xaa Xaa Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
     non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
     2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
     1-7 residues
<220> FEATURE:
<221> NAME/KEY: MOD_RES
```

<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 130

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa
            20                  25                  30

Xaa Xaa

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 131

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:

```
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His
<220> FEATURE:
<221> NAME/KEY: MOD_RES
<222> LOCATION: (31)..(34)
<223> OTHER INFORMATION: Any amino acid

<400> SEQUENCE: 132

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
```

```
<221> NAME/KEY: MOD_RES
<222> LOCATION: (31)..(34)
<223> OTHER INFORMATION: Any amino acid

<400> SEQUENCE: 133

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 134

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
```

```
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 135

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 136
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 136

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa Xaa
            20                  25                  30

Xaa Xaa

<210> SEQ ID NO 137
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
```

```
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 137

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid
```

```
<400> SEQUENCE: 138

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Xaa His Xaa Xaa
                20                  25                  30

Xaa Xaa

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 139

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa
                20                  25                  30

Xaa Xaa

<210> SEQ ID NO 140
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
```

<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 140

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa His Xaa Xaa
            20                  25                  30

Xaa Xaa

<210> SEQ ID NO 141
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 141

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa
            20                  25                  30

Xaa Xaa

```
<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 142

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
```

```
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 143

Xaa Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 144
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 144

Xaa Xaa Xaa Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 145
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 145

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa
            20                  25                  30

Xaa Xaa

<210> SEQ ID NO 146
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
```

```
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (31)..(34)
<223> OTHER INFORMATION: Any amino acid

<400> SEQUENCE: 146

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      non-canonical zinc finger component polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid except His or Cys
<220> FEATURE:
<221> NAME/KEY: MOD_RES
<222> LOCATION: (5)..(8)
<223> OTHER INFORMATION: Any amino acid and this region may encompass
      2-4 residues
<220> FEATURE:
<221> NAME/KEY: MOD_RES
<222> LOCATION: (9)..(9)
<223> OTHER INFORMATION: Any amino acid except His or Cys
<220> FEATURE:
<221> NAME/KEY: MOD_RES
<222> LOCATION: (10)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid except His or Cys
<220> FEATURE:
<221> NAME/KEY: MOD_RES
<222> LOCATION: (23)..(29)
<223> OTHER INFORMATION: Any amino acid and this region may encompass
      1-7 residues
<220> FEATURE:
<221> NAME/KEY: MOD_RES
<222> LOCATION: (30)..(30)
<223> OTHER INFORMATION: Any amino acid except His or Cys
<220> FEATURE:
<221> NAME/KEY: MOD_RES
<222> LOCATION: (31)..(34)
<223> OTHER INFORMATION: Any amino acid

<400> SEQUENCE: 147

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Xaa Xaa
                20                  25                  30
Xaa Xaa
```